United States Patent
Werneth et al.

(10) Patent No.: US 8,849,367 B2
(45) Date of Patent: Sep. 30, 2014

(54) RF ENERGY DELIVERY SYSTEM AND METHOD

(71) Applicant: Medtronic Ablation Frontiers LLC, Minneapolis, MN (US)

(72) Inventors: Randell L. Werneth, San Diego, CA (US); Ricardo D. Roman, Chula Vista, CA (US); Christopher G. Kunis, Escondido, CA (US); Alexander J. Asconeguy, Murrieta, CA (US); Sadaf Soleymani, Reseda, CA (US); Jeffrey Trinidad, San Diego, CA (US); Martin Chambers, Stillwater, MN (US); Hakan Oral, Ann Arbor, MI (US); Fred Morady, Ann Arbor, MI (US); Jerald L. Cox, Carlsbad, CA (US); Guillermo W. Moratorio, Cardiff by the Sea, CA (US); Samuel Fu, Carlsbad, CA (US); J. Christopher Flaherty, Topsfield, MA (US)

(73) Assignee: Medtronic Ablation Frontiers LLC, Minneapolis, MN (US)

(*) Notice: Subject to any disclaimer, the term of this patent is extended or adjusted under 35 U.S.C. 154(b) by 0 days.

(21) Appl. No.: 13/906,762

(22) Filed: May 31, 2013

(65) Prior Publication Data
US 2013/0296844 A1 Nov. 7, 2013

Related U.S. Application Data

(63) Continuation of application No. 12/332,236, filed on Dec. 10, 2008, now Pat. No. 8,475,449.

(60) Provisional application No. 61/007,016, filed on Dec. 10, 2007.

(51) Int. Cl.
 *A61B 5/04* (2006.01)
 *A61B 18/18* (2006.01)
 *A61B 18/14* (2006.01)
 *A61B 17/00* (2006.01)

(52) U.S. Cl.
 CPC .......... *A61B 18/18* (2013.01); *A61B 2017/003* (2013.01); *A61B 18/1492* (2013.01)
 USPC .............................. 600/372; 606/41; 606/129

(58) Field of Classification Search
 CPC ................ A61B 18/1492; A61B 2018/00214; A61B 2018/00267; A61B 2018/1467; A61B 2018/165
 USPC ........ 600/372–374; 606/32, 41, 129; 607/122
 See application file for complete search history.

(56) References Cited

U.S. PATENT DOCUMENTS

| | | | |
|---|---|---|---|
| 3,270,307 A | 8/1966 | Jean et al. | |
| 4,564,201 A | 1/1986 | Hannah | |

(Continued)

*Primary Examiner* — Nicholas Lucchesi
*Assistant Examiner* — Gerald Landry, II
(74) *Attorney, Agent, or Firm* — Christopher & Weisberg, P.A.

(57) ABSTRACT

Devices, systems and methods are disclosed for the ablation of tissue. A steerable ablation catheter can include one or more ablation elements at its distal end and one or more ablation elements fixedly attached to its shaft. The distal end of the ablation catheter can be deflected to assume a number of different deflection geometries in at least one direction along the shaft. One feature of the ablation catheter is that its shaft can comprise materials of differing durometers or stiffnesses attached together at a joint. Methods associated with use of the ablation catheter are also covered.

1 Claim, 24 Drawing Sheets

(56) References Cited

U.S. PATENT DOCUMENTS

| | | | |
|---|---|---|---|
| 5,052,105 A | 10/1991 | Mische et al. | |
| 5,257,451 A | 11/1993 | Edwards et al. | |
| 5,389,073 A | 2/1995 | Imran | |
| 5,411,025 A * | 5/1995 | Webster, Jr. | 600/374 |
| 5,826,576 A | 10/1998 | West | |
| 5,895,378 A | 4/1999 | Nita | |
| 5,916,158 A * | 6/1999 | Webster, Jr. | 600/374 |
| 6,165,172 A * | 12/2000 | Farley et al. | 606/33 |
| 2001/0001314 A1 * | 5/2001 | Davison et al. | 606/41 |
| 2002/0111618 A1 | 8/2002 | Stewart et al. | |
| 2006/0095022 A1 | 5/2006 | Moll et al. | |
| 2006/0095105 A1 * | 5/2006 | Jog et al. | 607/116 |
| 2008/0039916 A1 * | 2/2008 | Colliou et al. | 607/116 |
| 2008/0125772 A1 * | 5/2008 | Stone et al. | 606/41 |
| 2008/0139913 A1 * | 6/2008 | Schulman | 600/395 |
| 2010/0049191 A1 * | 2/2010 | Habib et al. | 606/41 |

* cited by examiner

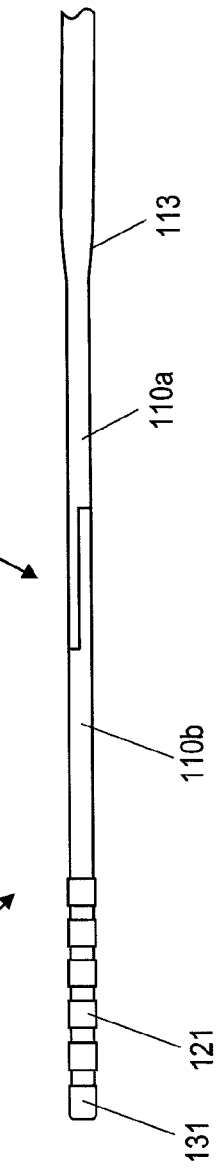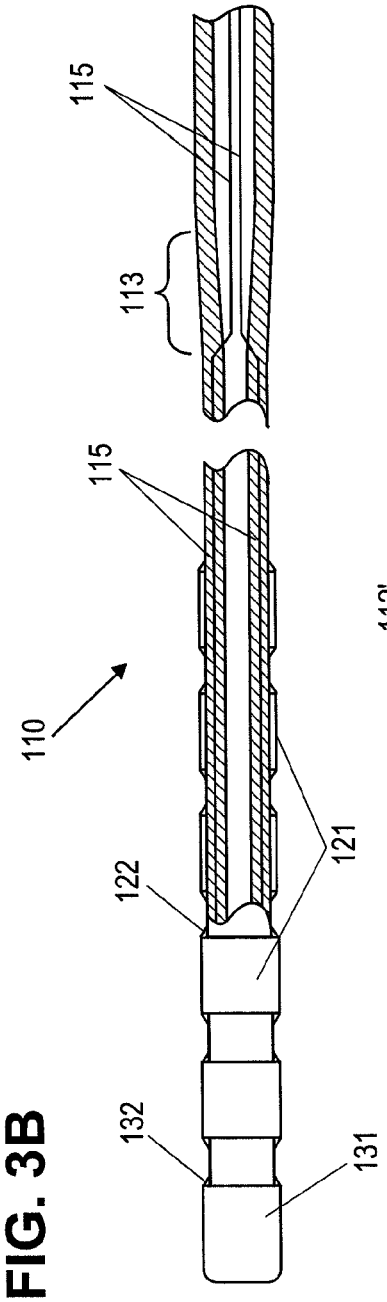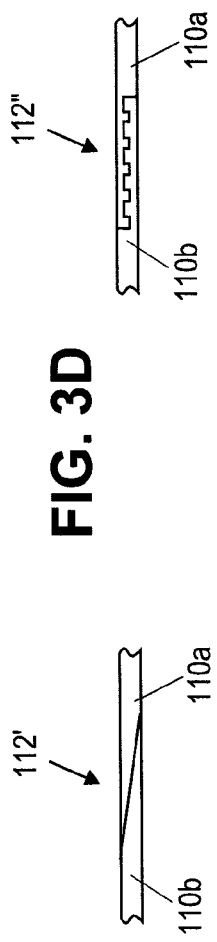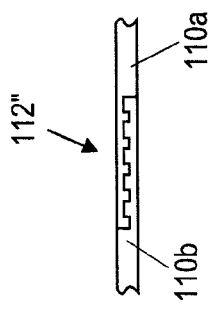
FIG. 3A
FIG. 3B
FIG. 3C
FIG. 3D

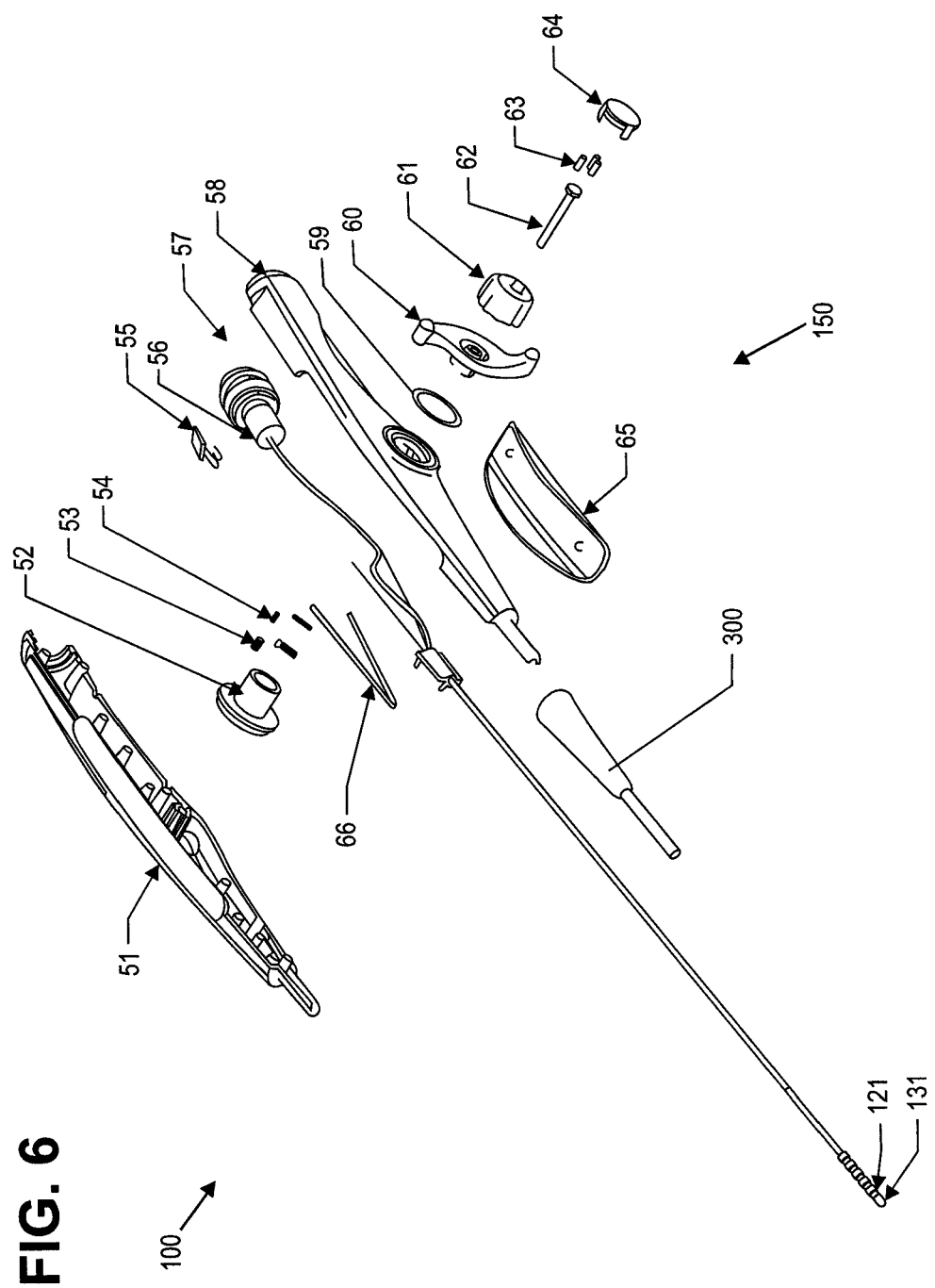

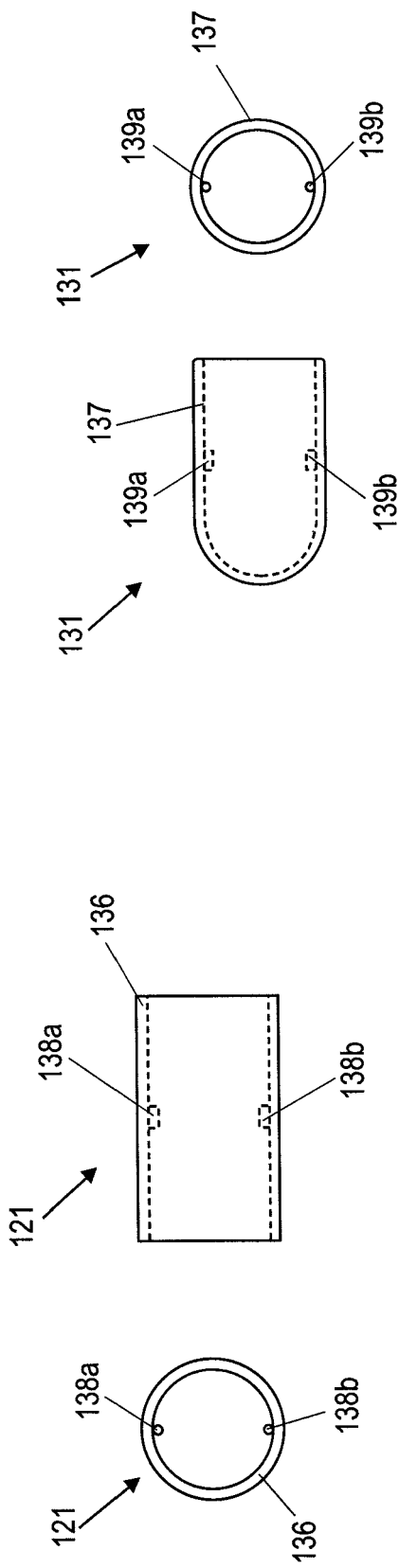

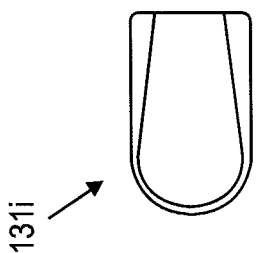
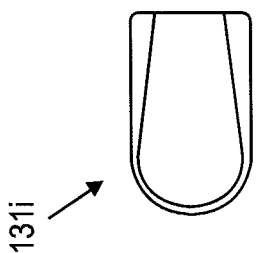
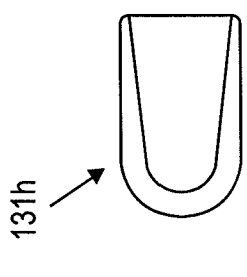
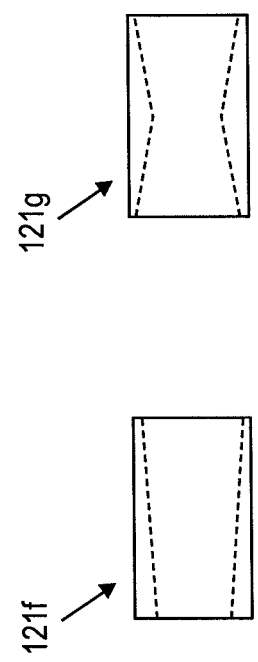
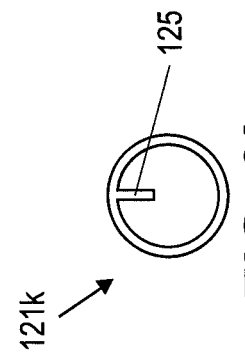
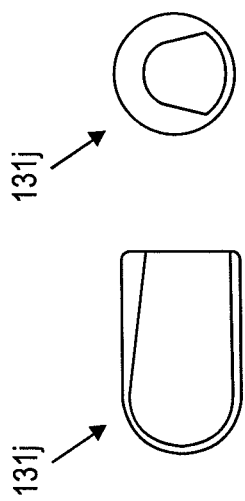
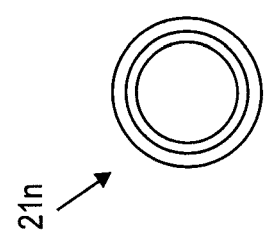
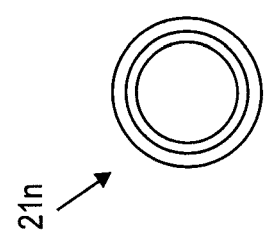
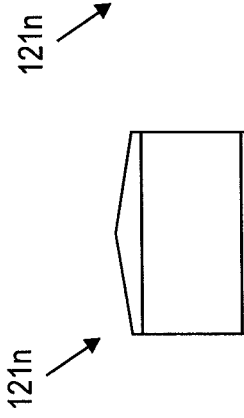
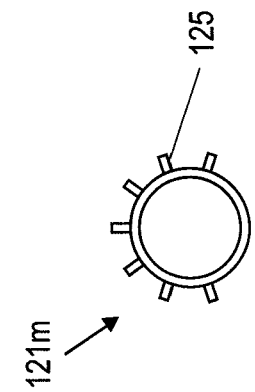

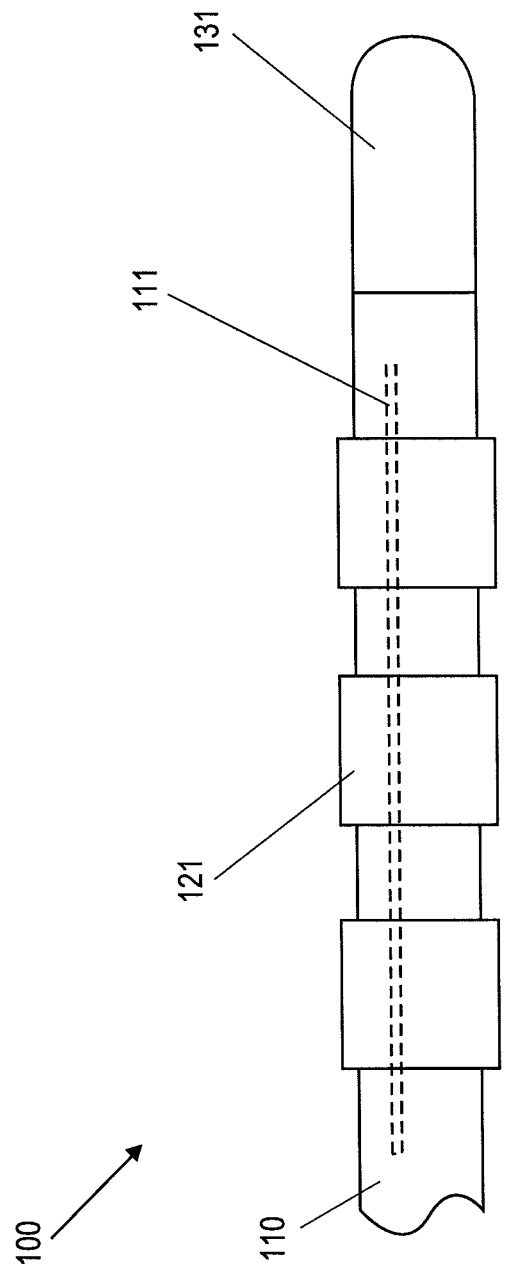

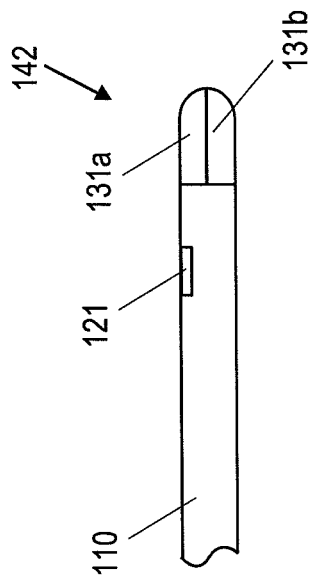
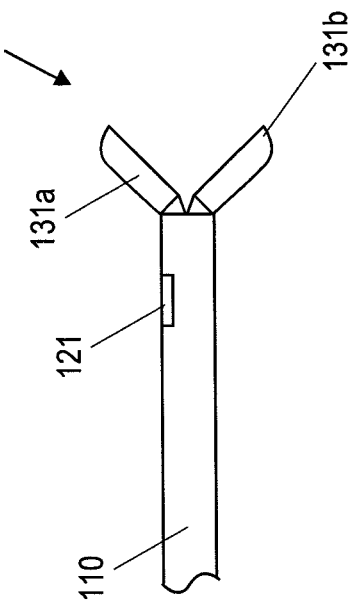
FIG. 11A    FIG. 11B
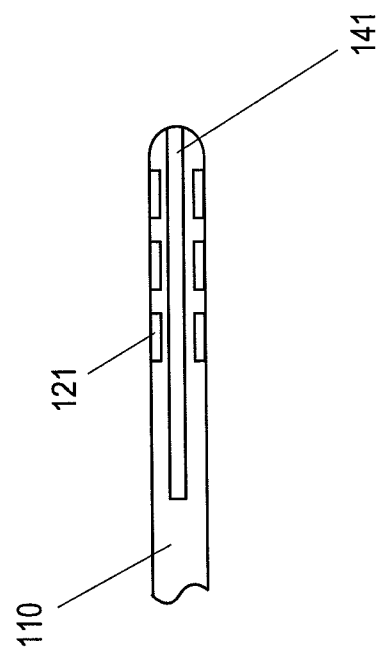
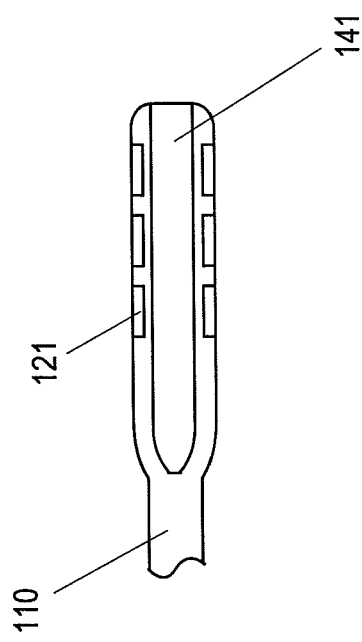
FIG. 12A    FIG. 12B

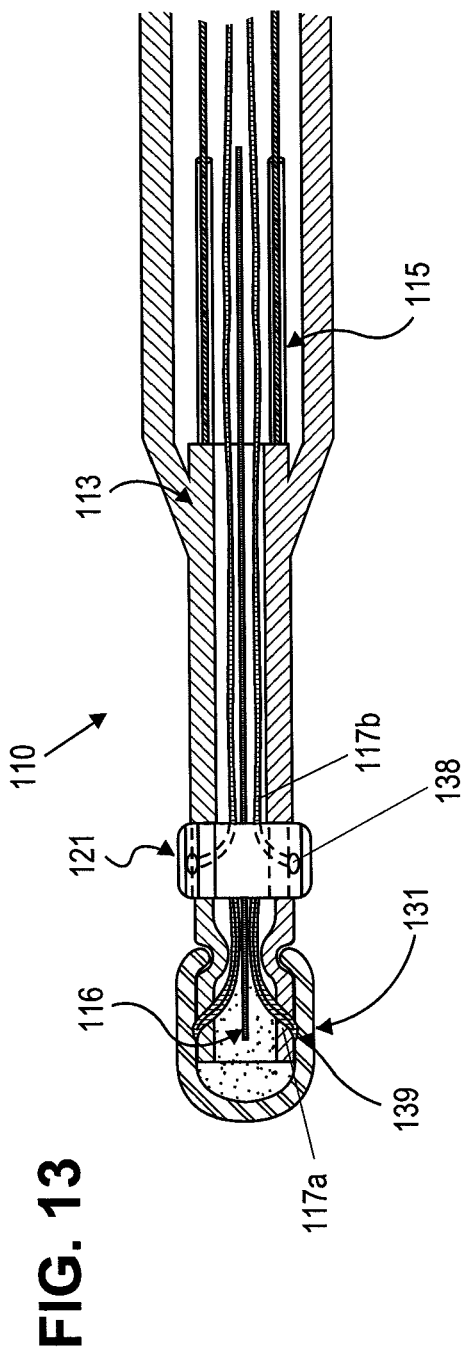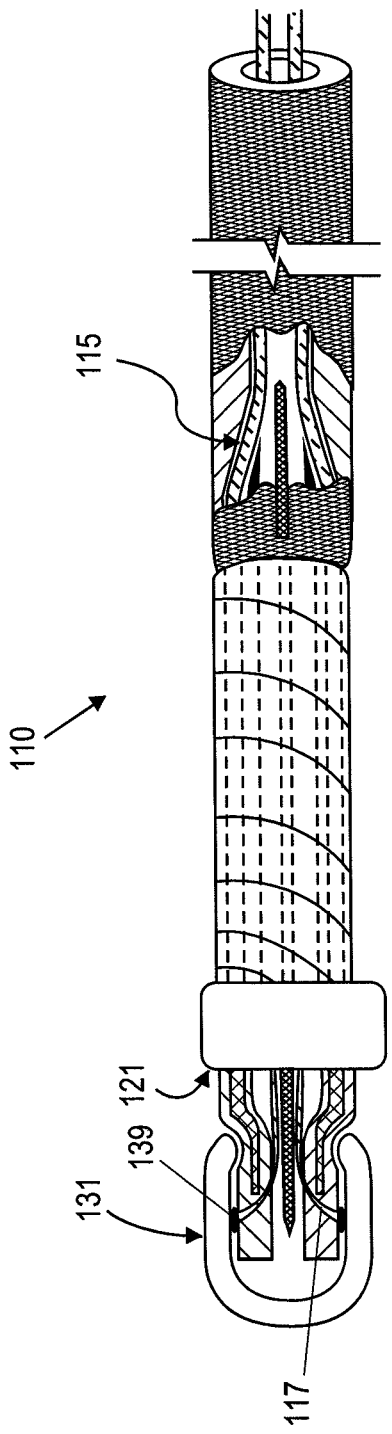
FIG. 13
FIG. 14

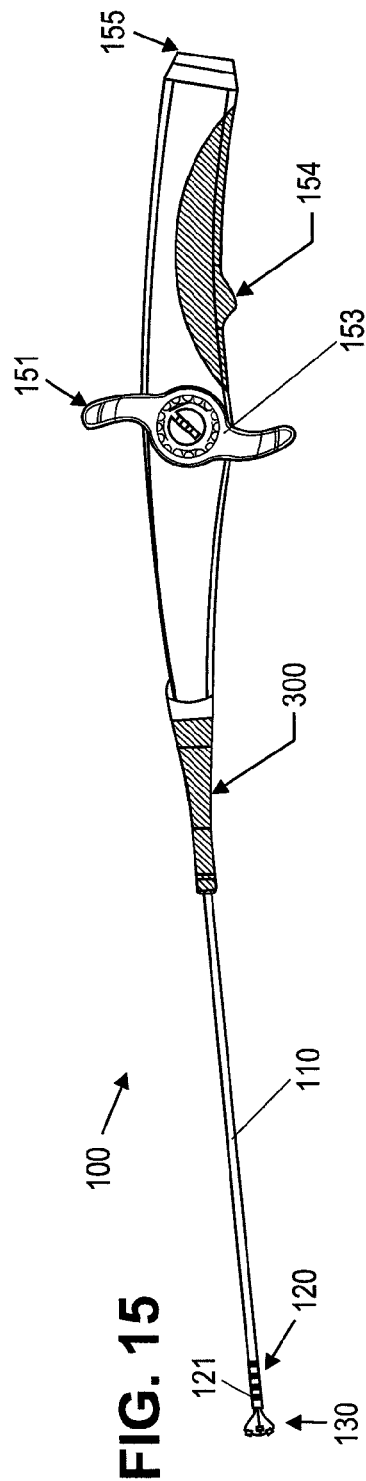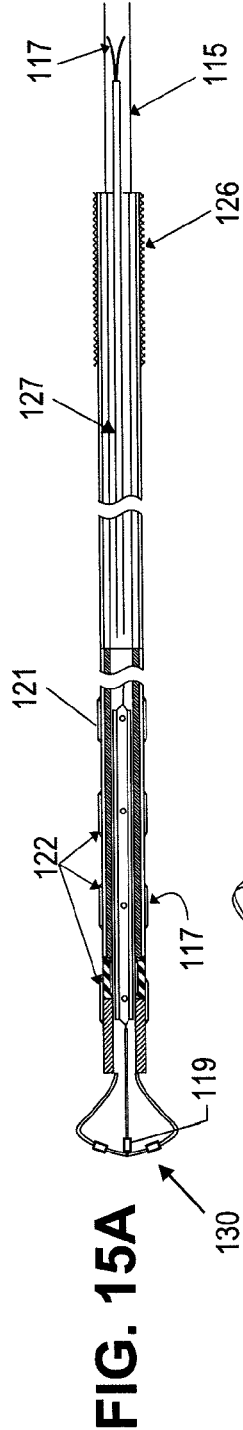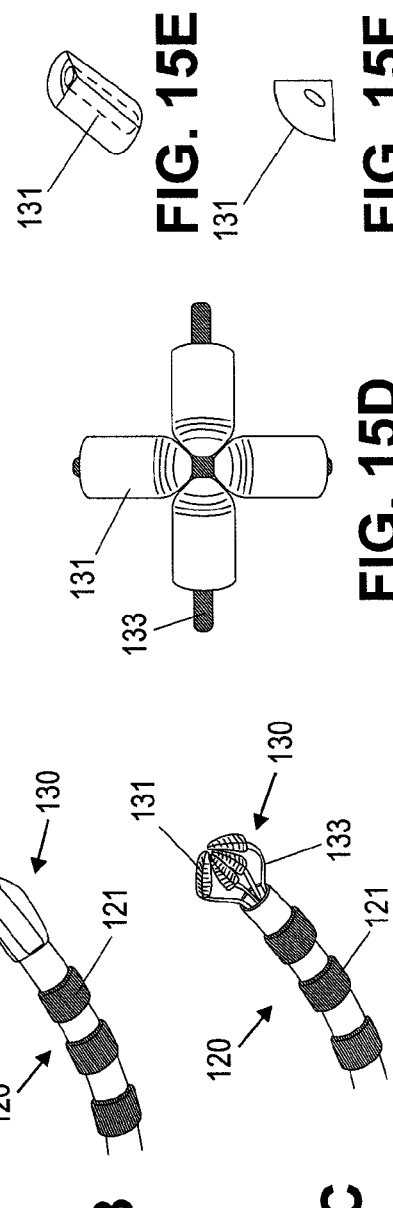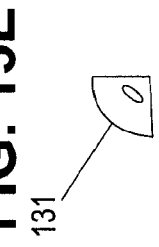
FIG. 15  FIG. 15A  FIG. 15B  FIG. 15C  FIG. 15D  FIG. 15E  FIG. 15F

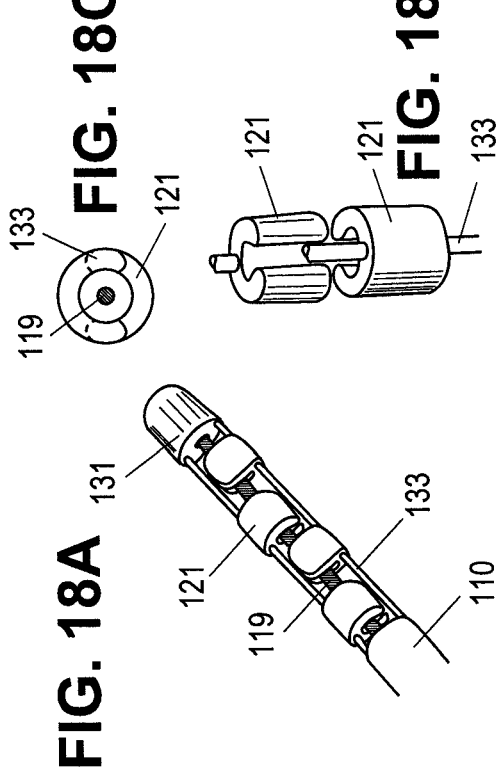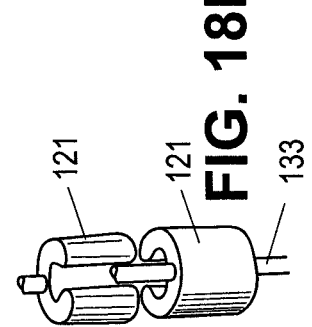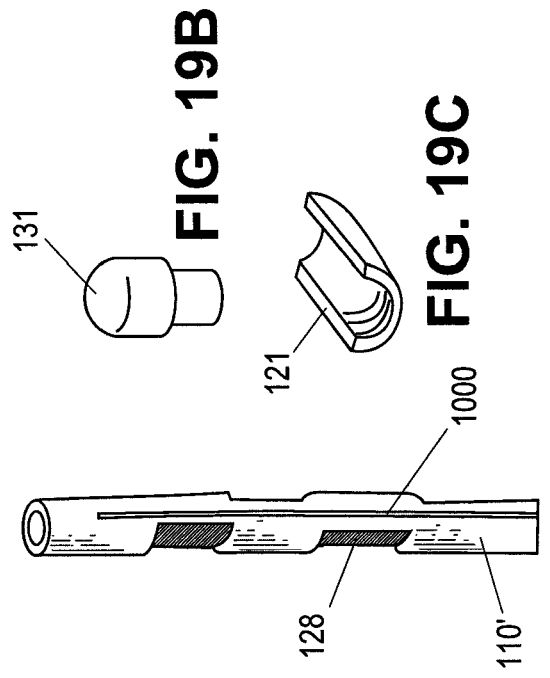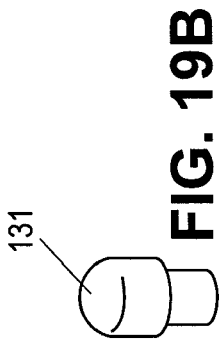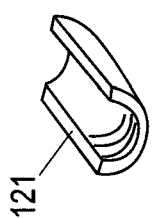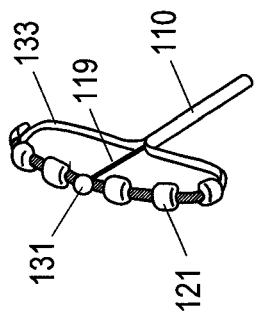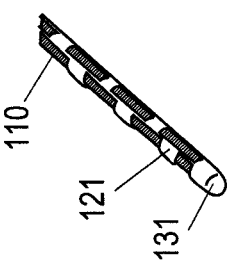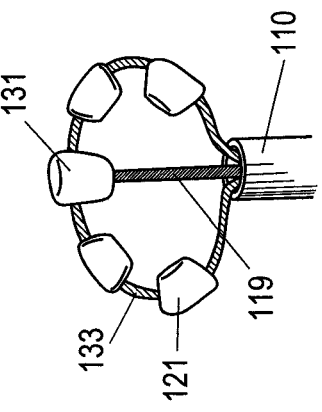

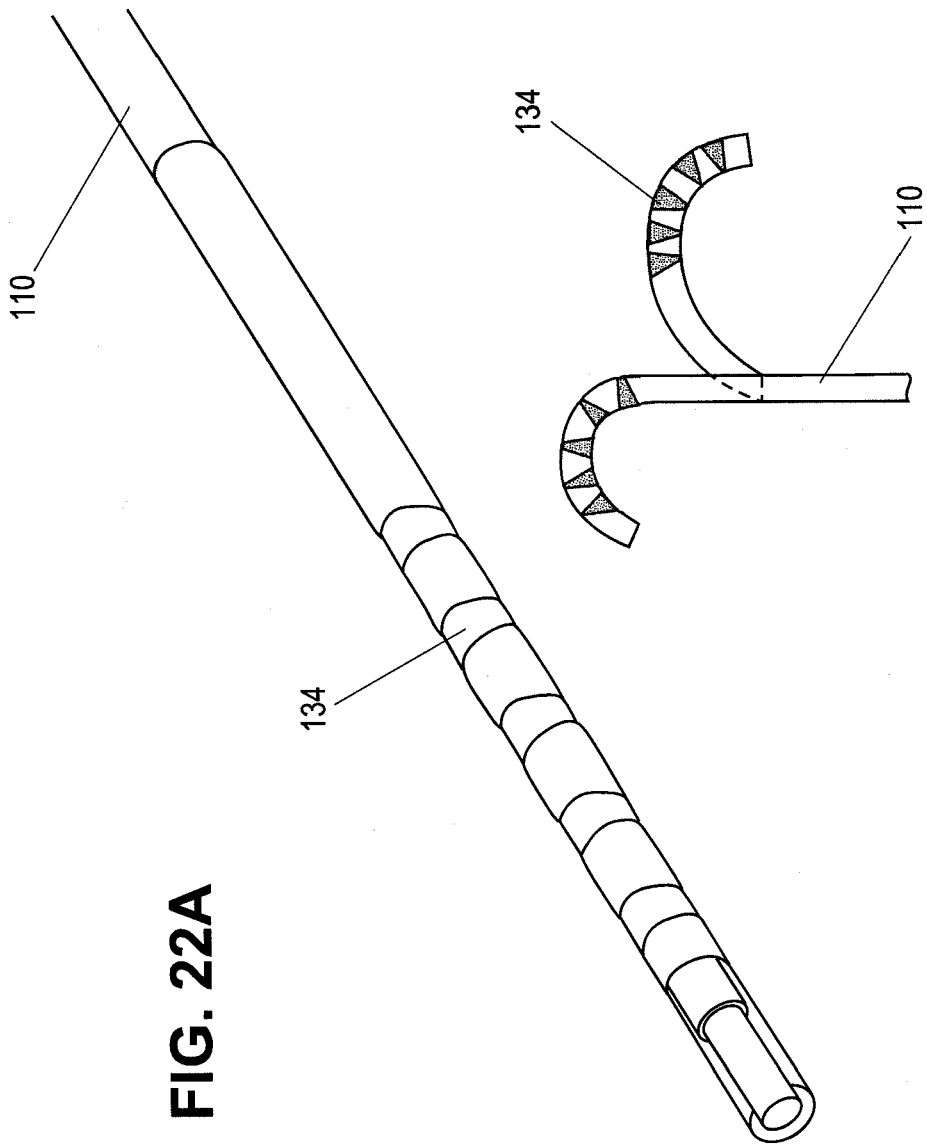

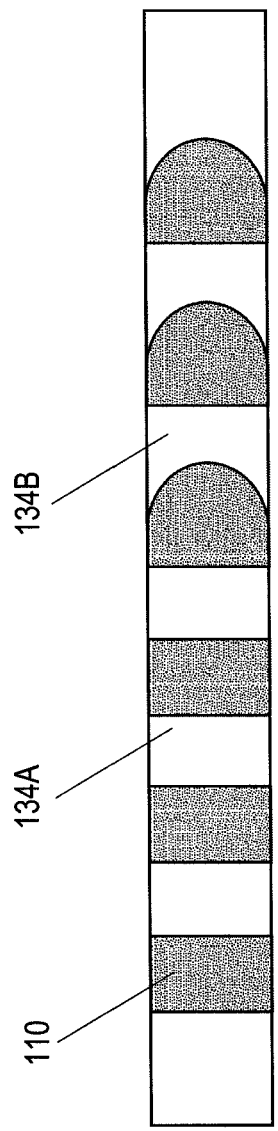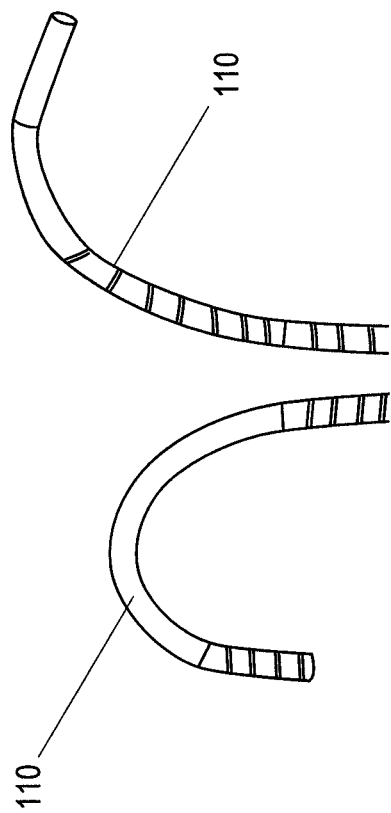

RF ENERGY DELIVERY SYSTEM AND METHOD

CROSS-REFERENCE TO RELATED APPLICATION

This application is a continuation of, and claims priority to, U.S. patent application Ser. No. 12/332,236, filed Dec. 10, 2008, entitled RF ENERGY DELIVERY SYSTEM AND METHOD, which application claims the benefit of U.S. Provisional Application No. 61/007,016, filed Dec. 10, 2007, the entirety of both of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to ablation systems and methods for performing targeted tissue ablation in a patient. In particular, the present invention provides catheters which deliver radiofrequency (RF) energy that create safe, precision lesions in tissue such as linear lesions created in cardiac tissue.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia condition. Often the ablation is performed by passing energy, such as electrical energy, through one or more electrodes and causing the tissue in contact with the electrodes to heat up to an ablative temperature. Ablation procedures can be performed on patients with atrial fibrillation (AF) by ablating tissue in the heart.

Mammalian organ function typically occurs through the transmission of electrical impulses from one tissue area to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated atrial contractions that result in ineffective pumping of blood into the ventricle as well as a lack of synchrony. During AF, the atrioventricular node receives electrical impulses from numerous locations throughout the atria instead of only from the sinus node. These aberrant signals overwhelm the atrioventricular node, producing an irregular and rapid heartbeat. As a result, blood may pool in the atria, increasing the likelihood of blood clot formation. The major risk factors for AF include age, coronary artery disease, rheumatic heart disease, hypertension, diabetes, and thyrotoxicosis. AF affects 7% of the population over age 65.

Atrial fibrillation treatment options are limited. Lifestyle changes only assist individuals with lifestyle related AF. Medication therapy manages AF symptoms, often presents side effects more dangerous than AF, and fails to cure AF. Electrical cardioversion attempts to restore a normal sinus rhythm, but has a high AF recurrence rate. In addition, if there is a blood clot in the atria, cardioversion may cause the clot to leave the heart and travel to the brain (causing a stroke) or to some other part of the body. What are needed are new methods for treating AF and other medical conditions involving disorganized electrical conduction.

Various ablation techniques have been proposed to treat AF, including the Cox-Maze ablation procedure, linear ablation of various regions of the atrium, and circumferential ablation of pulmonary vein ostia. The Cox-Maze ablation procedure and linear ablation procedures are tedious and time-consuming, taking several hours to accomplish. Current pulmonary vein ostial ablation is proving to be difficult to do, and has lead to rapid stenosis and potential occlusion of the pulmonary veins. All ablation procedures involve the risk of inadvertently damaging untargeted tissue, such as the esophagus while ablating tissue in the left atrium of the heart. There is therefore a need for improved atrial ablation products and techniques that create efficacious lesions in a safe manner.

SUMMARY OF THE INVENTION

Several unique ablation catheters and ablation catheter systems and methods are provided which map and ablate surface areas within the heart chambers of a patient, with one or few catheter placements. Any electrocardiogram signal site (e.g. a site with aberrant signals) or combination of multiple sites that are discovered with this placement may be ablated. In alternative embodiments, the ablation catheters and systems may be used to treat non-cardiac patient tissue, such as tumor tissue.

According to a first aspect of the invention, an ablation catheter for performing a medical procedure on a patient is provided. The ablation catheter comprises an elongate shaft with a proximal portion including a proximal end and a distal end, and a distal portion with a proximal end and a distal end. The elongate shaft further comprises a shaft ablation assembly and a distal ablation assembly configured to deliver energy, such as RF energy, to tissue. The shaft ablation assembly is proximal to the distal end of the distal portion, and includes at least one shaft ablation element fixedly attached to the shaft and configured to deliver ablation energy to tissue. The distal ablation assembly is at the distal end of the distal portion and includes at least one tip ablation element configured to deliver ablation energy to tissue.

In a preferred embodiment, the distal portion can be deflected in one or more directions, in one or more deflection geometries. The deflection geometries may be similar or symmetric deflection geometries, or the deflection geometries may be dissimilar or asymmetric deflection geometries. The shaft may include one or more steering wires configured to deflect the distal portion in the one or more deflection directions. The elongate shaft may include different diameters along its length, and the stiffness of the shaft may vary along its length. The elongate shaft may include a guide plate within the shaft, the guide plate configured to enhance the deflection (steering) of the distal portion, such as to maintain deflections in a single plane. The shaft may include variable material properties such as a asymmetric joint between two portions, an integral member within a wall or fixedly attached to the shaft, a variable braid, or other variation used to create multiple deflections, such as deflections with asymmetric deflection geometries.

In another preferred embodiment, the distal ablation assembly may be fixedly attached to the distal end of the distal portion, or it may be advanceable from the distal portion, such as via a control shaft. The distal ablation assembly may comprise a single ablation element, such as an electrode, or multiple ablation elements. The distal ablation assembly may include a carrier assembly of ablation elements, and the carrier assembly may be changeable from a compact geometry to an expanded geometry, such transition caused by advancement and/or retraction of a control shaft. The distal ablation assembly may include multiple ablation elements which can be positioned to grab and/or surround a portion of tissue, such as ablation elements on forked or scissor carrier arms.

The shaft ablation assembly may include a single ablation element or multiple ablation elements, preferably three to six ablation elements fixedly attached to the shaft. The ablation elements may have a profile that is flush with the surface of the shaft, or more preferably the ablation elements outer diameter is slightly greater than the shaft diameter such that the ablation elements have improved contact with tissue during delivery of ablation energy.

The ablation elements of the present invention can deliver one or more forms of energy, preferably RF energy. The ablation elements may have similar or dissimilar construction, and may be constructed in various sizes and geometries. The ablation elements may include one or more thermocouples, such as two thermocouples mounted 180° from each other on an ablation element inner or outer surface. The ablation elements may include means of dissipating heat, such as increased surface area of projecting fins. The ablation elements may have asymmetric geometries, such as electrodes with thin and thick walls positioned on the inside and/or outside of one or more curved deflection geometries. In a preferred embodiment, one or more ablation elements is configured in a tubular geometry, and the wall thickness to outer diameter approximates a 1:10 ratio. In another preferred embodiment, one or more ablation elements is configured to record, or map electrical activity in tissue such as mapping of cardiac electro grams. In yet another preferred embodiment, one or more ablation elements is configured to deliver pacing energy, such as to energy delivered to pace the heart of a patient.

The ablation catheters of the present invention may be used to treat one or more medical conditions by delivering ablation energy to tissue. Conditions include an arrhythmia of the heart, cancer, and other conditions in which removing or denaturing tissue improves the patient's health.

According to another aspect of the invention, a kit of ablation catheters is provided. A first ablation catheter has a distal portion which can be deflected in at least two symmetric geometries. A second ablation catheter has a distal portion which can be deflected in at least two asymmetric geometries.

According to another aspect of the invention, a method of treating proximal or chronic atrial fibrillation is provided. An ablation catheter of the present invention may be placed in the coronary sinus of the patient, such as to map electrograms and/or ablate tissue, and subsequently placed in the left or right atrium to ablate tissue. The ablation catheter may be placed to ablate one or more tissue locations including but not limited to: fasicals around a pulmonary vein; and the mitral isthmus.

According to another aspect of the invention, a method of treating atrial flutter is provided. An ablation catheter of the present invention may be used to achieve bi-directional block, such as by placement in one or more locations in the right atrium of the heart.

According to another aspect of the invention, a method of ablating tissue in the right atrium of the heart is provided. An ablation catheter of the present invention may be used to: create lesions between the superior vena cava and the inferior vena cava; the coronary sinus and the inferior vena cava; the superior vena cava and the coronary sinus; and combinations of these. The catheter can be used to map and/or ablate the sinus node, such as to treat sinus node tachycardia.

According to another aspect of the invention, a method of treating ventricular tachycardia is provided. An ablation catheter of the present invention may be placed in the left or right ventricles of the heart, induce ventricular tachycardia by delivering pacing energy, and ablating tissue to treat the patient.

According to another aspect of the invention, an ablation catheter with a first deflection geometry larger than a second deflection geometry is provided. The ablation catheter is placed in the smaller second deflection geometry to ablate one or more of the following tissue locations: left atrial roof; left atrial septum; tissue adjacent the left atrial septum; and tissue adjacent the left atrial posterior wall. The ablation catheter is placed in the larger first deflection geometry to ablate at least the left atrial floor.

According to another aspect of the invention, an ablation catheter of the present invention is used to treat both the left and right atria of a heart. The catheter is configured to transition to a deflection geometry with a first deflection geometry and a second deflection geometry, where the first deflection geometry is different than the second deflection geometry. The catheter is used to ablate tissue in the right atrium using at least the first deflection geometry and also ablate tissue in the left atrium using at least the second deflection geometry.

According to a first aspect of the invention, a catheter for performing a medical procedure on a patient is provided. The catheter comprises an elongate shaft with a proximal portion including a proximal end and a distal end, and a distal portion with a proximal end and a distal end. The catheter further comprises a deflection assembly configured to deflect the distal portion in a first direction in a first geometry and a second direction in a second geometry, wherein the first and second geometries are different. The catheter further includes a functional element fixedly mounted to the distal portion.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

FIG. 3A illustrates a side view of the distal portion of a shaft of an ablation catheter, with a staircase joint, consistent with the present invention.

FIG. 3B illustrates a side, partial sectional view of the shaft of FIG. 3A.

FIG. 3C illustrates a side view of an alternative tapered joint, consistent with the present invention.

FIG. 3D illustrates a side view of an alternative toothed joint, consistent with the present invention.

FIG. 6 is an exploded view of a handle of an ablation catheter, consistent with the present invention.

FIGS. 7A and 7B illustrate end and side views, respectively, of a preferred shaft electrode, consistent with the present invention.

FIGS. 7C and 7D illustrate side and end views, respectively, of a preferred tip electrode, consistent with the present invention.

FIG. 7E illustrates a side sectional view of the distal end of a catheter shaft, consistent with the present invention.

FIGS. 9E and 9F illustrate side views of a preferred configuration of two shaft electrodes, each with non-uniform wall thickness, consistent with the present invention.

FIGS. 9G and 9H illustrate side views of a preferred configuration of two tip electrodes, each with non-uniform wall thickness, consistent with the present invention.

FIGS. 9J and 9K illustrate side and end views, respectively, of a preferred configuration of a tip electrode with eccentric wall thickness, consistent with the present invention.

FIG. 9L illustrates an end view of a preferred configuration of a shaft electrode, with a projecting fin, consistent with the present invention.

FIG. 9M illustrates an end view of a preferred configuration of a shaft electrode, with multiple projecting fins, consistent with the present invention.

FIGS. 9N and 9P illustrate side and end views, respectively, of a preferred configuration of a shaft electrode, with non-uniform wall thickness, consistent with the present invention.

FIG. 10 illustrates a side view of the distal portion of an ablation catheter, with a malleable member incorporated into the shaft, consistent with the present invention.

FIGS. 11A and 11B illustrate side views of the distal portion of an ablation catheter, in unexpanded and expanded states, respectively, consistent with the present invention.

FIGS. 12A and 12B illustrate side views of the distal portion of an ablation catheter, in undeployed and deployed states, respectively, consistent with the present invention.

FIG. 13 illustrates a side sectional view of the distal portion of an ablation catheter, consistent with the present invention.

FIG. 14 illustrates a side sectional view of the distal portion of an ablation catheter, consistent with the present invention.

FIGS. 15, 15A, 15B, 15C, 15D, 15E and 15F illustrate numerous views of an ablation catheter including a carrier assembly advanceable from the distal end of the shaft, consistent with the present invention.

FIGS. 18A, 18B, 18C and 18D illustrate various views of the distal portion of an ablation catheter including an expandable carrier assembly, consistent with the present invention.

FIGS. 19A, 19B, 19C, 19D and 19E illustrate various views of the distal portion of an ablation catheter including an expandable split shaft, consistent with the present invention.

FIG. 22A illustrates a perspective view of the distal portion of an asymmetrically deflectable catheter shaft construction including one or more wedges, consistent with the present invention.

FIG. 22B illustrates two unique bending geometries of the catheter shaft of FIG. 22A.

FIG. 23A illustrates a side view of the distal portion of an asymmetrically deflectable catheter shaft construction including one or more wedges, consistent with the present invention.

FIGS. 23B and 23C illustrate two unique bending geometries of the catheter shaft of FIG. 23A.

DETAILED DESCRIPTION OF THE INVENTION

Figure 1:
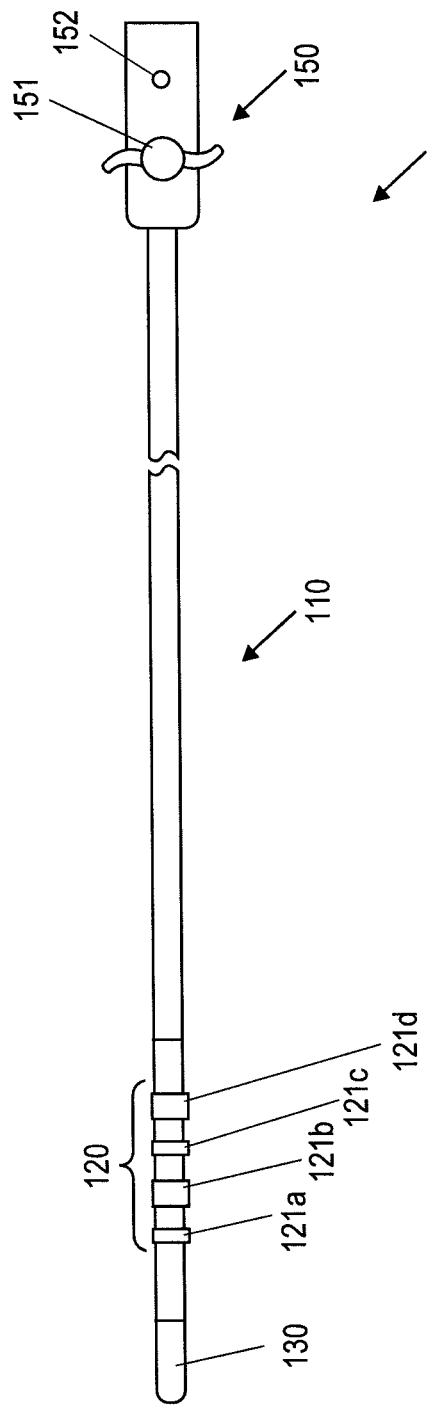
FIG. 1 illustrates a side view of an ablation catheter, consistent with the present invention.

Certain specific details are set forth in the following description and figures to provide an understanding of various embodiments of the invention. Certain well-known details, associated electronics and devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

The present invention provides catheters for performing targeted tissue ablation in a subject. In preferred embodiments, the catheters comprise an elongate shaft having a proximal end and distal end and preferably a lumen extending at least partially therebetween. The catheter is preferably of the type used for performing intracardiac procedures, typically being introduced from the femoral vein in a patient's leg or from a vessel in the patient's neck. The catheter is preferably introducible through a sheath, such as a transeptal sheath, and also preferably has a steerable tip that allows positioning of the distal portion such as when the distal end of the catheter is within a heart chamber. The catheters include ablation elements located at the distal end of the shaft (tip electrodes), as well as ablation elements located on an exterior surface of the shaft proximal to the distal end (shaft electrodes). The tip electrodes may be fixedly attached to the distal end of the shaft, or may be mounted on an advanceable and/or expandable carrier assembly. The carrier assembly may be attached to a control shaft that is coaxially disposed and slidingly received within the lumen of the shaft. The carrier assembly is deployable by activating one or more controls on a handle of the catheter, such as to engage one or more ablation elements against cardiac tissue, typically atrial wall tissue or other endocardial tissue. The shaft may include deflection means, such as means operably connected to a control on a handle of the catheter. The deflection means may deflect the distal portion of the shaft in one or more directions, such as deflections with two symmetric geometries, two asymmetric geometries, or combinations of these. Asymmetries may be caused by different radius of curvature, different length of curvature, differences in planarity, other different 2-D shapes, other different 3-D shapes, and the like.

In particular, the present invention provides ablation catheters with multiple electrodes that provide electrical energy, such as radiofrequency (RF) energy, in monopolar (unipolar), bipolar or combined unipolar-bipolar fashion, as well as methods for treating conditions such as paroxysmal atrial fibrillation, chronic atrial fibrillation, atrial flutter, supra ventricular tachycardia, atrial tachycardia, ventricular tachycardia, ventricular fibrillation, and the like, with these devices.

The normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters and RF generators of the present invention may be employed.

One current method of treating cardiac arrhythmias is with catheter ablation therapy. Physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician) directs a catheter through a main vein or artery into the interior region of the heart that is to be treated. The ablating element (or elements) is next placed near the targeted cardiac tissue that is to be ablated. The physician directs energy, provided by a source external to the patient, from one ore more ablation elements to ablate the neighboring tissue and form a lesion. In general, the goal of catheter ablation therapy is to disrupt the electrical pathways in cardiac tissue to stop the emission and/or prevent the propagation of erratic electric impulses, thereby curing the focus of the disorder. For treatment of AF, currently available methods and devices have shown only limited success and/or employ devices that are extremely difficult to use or otherwise impractical.

The ablation systems of the present invention allow the generation of lesions of appropriate size and shape to treat conditions involving disorganized electrical conduction (e.g., AF). The ablation systems of the present invention are also practical in terms of ease-of-use and limiting risk to the patient (such as in creating an efficacious lesion while minimizing damage to untargeted tissue), as well as significantly reducing procedure times. The present invention addresses this need with, for example, arrangements of one or more tip ablation elements and one or more shaft ablation elements configured to create a linear lesion in tissue, such as the endocardial surface of a chamber of the heart, by delivery of energy to tissue or other means. The electrodes of the present invention may include projecting fins or other heat dissipating surfaces to improve cooling properties. The distal portions of the catheter shafts of the present invention may deflect in two or more symmetric or asymmetric geometries, such as asymmetric geometries with different radius of curvature or other geometric shape differences. The ablation catheters and RF generators of the present invention allow a clinician to treat a patient with AF in a procedure much shorter in duration than current AF ablation procedures. The lesions created by the ablation catheters and RF generators of the present invention are suitable for inhibiting the propagation of inappropriate electrical impulses in the heart for prevention of reentrant arrhythmias, while minimizing damage to untargeted tissue, such as the esophagus or phrenic nerve of the patient.

DEFINITIONS

To facilitate an understanding of the invention, a number of terms are generally defined below.

As used herein, the terms "subject" and "patient" refer to any animal, such as a mammal like livestock, pets, and preferably a human. Specific examples of "subjects" and "patients" include, but are not limited, to individuals requiring medical assistance, and in particular, requiring AF catheter ablation treatment.

As used herein, the terms "catheter ablation" or "ablation procedures" or "ablation therapy," and like terms, refer to what is generally known as tissue destruction procedures. Ablation is often used in treating several medical conditions, including abnormal heart rhythms. It can be performed both surgically and non-surgically. Non-surgical ablation is typically performed in a special lab called the electrophysiology (EP) laboratory. During this non-surgical procedure an ablation catheter is inserted into the heart using fluoroscopy for visualization, and then an energy delivery apparatus is used to direct energy to the heart muscle via one or more ablation elements of the ablation catheter. This energy either "disconnects" or "isolates" the pathway of the abnormal rhythm (depending on the type of ablation). It can also be used to disconnect the conductive pathway between the upper chambers (atria) and the lower chambers (ventricles) of the heart. For individuals requiring heart surgery, ablation can be performed during coronary artery bypass or valve surgery.

As used herein, the term "ablation element" refers to an energy delivery element, such as an electrode for delivering electrical energy. Ablation elements can be configured to deliver multiple types of energy, such as ultrasound energy and cryogenic energy, either simultaneously or serially. Electrodes can be constructed of a conductive plate, cylinder or tube, a wire coil, or other means of conducting electrical energy through contacting tissue. In unipolar energy delivery, the energy is conducted from the electrode, through the tissue to a ground pad, such as a conductive pad attached to the back of the patient. The high concentration of energy at the electrode site causes localized tissue ablation. In bipolar energy delivery, the energy is conducted from a first electrode to one or more separate electrodes, relatively local to the first electrode, through the tissue between the associated electrodes. Bipolar energy delivery results in more precise, shallow lesions while unipolar delivery results in deeper lesions. Both unipolar and bipolar deliveries provide advantages, and the combination of their use is a preferred embodiment of this application.

As used herein, the term "carrier assembly" refers to a flexible carrier, on which one or more ablation elements are disposed. Carrier assemblies are not limited to any particular size, or shape, and can be configured to be constrained within an appropriately sized lumen.

As used herein, the term "carrier arm" refers to a wire-like shaft capable of interfacing with electrodes and coupling to an advanceable and/or retractable control shaft. A carrier arm is not limited to any size or measurement. Examples include, but are not limited to: stainless steel and other steel shafts; Nitinol shafts; titanium shafts; polyurethane shafts; and nylon shafts. Carrier arms can be entirely flexible, or may include flexible and rigid segments. Carrier arms may be radiopaque and/or include radiopaque or other visible markers, such as a marker used to identify a particular carrier arm.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein, the term "coagulum" refers to a blood mass or clot, such as a clot which may be caused by excessive heating in blood.

As used herein, the term "return pad" refers to a surface electrode mounted to the patient's body, typically on the patient's back. The return pad receives the RF ablation currents generated during unipolar power delivery. The return pad is sized (large enough) such that the high temperatures generated remain within a few millimeters of the specific ablation catheter's electrode delivering the unipolar power.

As used herein, the term "RF output" refers to an electrical output produced by the RF generator of the present invention. The RF output is electrically connected to a jack or other electro-mechanical connection means which allows electrical connection to one or more ablation elements (e.g. electrodes) of an ablation catheter. The RF output provides the RF energy to the ablation element to ablate tissue with bipolar and/or unipolar energy.

As used herein, the term "channel" refers to a pair of RF outputs between which bipolar energy is delivered. Each of the RF outputs in a channel may also deliver unipolar energy (simultaneous and/or sequential to bipolar energy delivery), such as when a return pad is connected.

As used herein, the term "targeted tissue" refers to tissue to be ablated, as identified by the clinician and/or one or more algorithms (e.g. algorithms of the system or algorithms otherwise available to the clinician). Lesions created in targeted tissue disconnect an aberrant electrical pathway causing an arrhythmia, or treat other undesired tissue such as cancer tissue.

As used herein, the term "untargeted tissue" refers to tissue which is desired to avoid damage by ablation energy, such as the esophagus or phrenic nerve in an arrhythmia ablation procedure.

As used herein, the term "power delivery scheme" refers to a set of ablation parameters to be delivered during a set ablation time, and used to safely create an effective lesion in targeted tissue. Power delivery scheme parameters include but are not limited to: type (bipolar and/or unipolar) of energy delivered; voltage delivered; current delivered; frequency of energy delivery; duty cycle parameter such as duty cycle percentage or length of period; field parameter such as configuration of fields or number of fields in set that repeats; and combinations thereof.

As used herein, the term "proximate" is used to define a particular location, such as "ablating tissue proximate the sinus node". For the purpose of this application, proximate shall include the area neighboring a target as well as the target itself. For the example above, the tissue receiving the ablation energy would be tissue neighboring the sinus node as well as the sinus node itself.

As used herein, the term "radius of curvature" is used to define the radius of a curved section of a deflectable distal portion of an ablation catheter. Deflectable distal portions may include complex curves, wherein the radius of curvature is an approximation of the curve of the entire distal portion when deflected. Distal portions may deflect in multiple planes, and the radius of curvature may represent the approximate radius when the multi-planar deflection is projected onto a single plane.

The present invention provides structures that embody aspects of the ablation catheter. The present invention also provides RF generators for providing ablation energy to the ablation catheters. The illustrated and preferred embodiments discuss these structures and techniques in the context of catheter-based cardiac ablation. These structures, systems, and techniques are well suited for use in the field of cardiac ablation.

However, it should be appreciated that the invention is applicable for use in other tissue ablation applications such as tumor ablation procedures. For example, the various aspects of the invention have application in procedures for ablating tissue in the prostrate, brain, gall bladder, uterus, and other regions of the body, preferably regions with an accessible wall or flat tissue surface, using systems that are not necessarily catheter-based. In a preferred embodiment, the target tissue is tumor tissue.

The ablation catheters and systems of the present invention have advantages over previous prior art devices. FIGS. 1-26 show various preferred embodiments of the ablation catheters and systems of the present invention. The present invention is not limited to these particular configurations.

Referring now to FIG. 1, one embodiment of an ablation catheter of the present invention is illustrated. Ablation catheter 100 includes flexible shaft 110. Handle 150 can be located on a proximal end the shaft and can include multiple controls, such as knob 151 and button 152. Button 152 can be configured to initiate and/or discontinue delivery of energy to one or more ablation elements located in a distal portion of the shaft. Knob 151 can be configured, when rotated, to cause the distal portion to deflect in one or more directions, such as to curve in one direction when rotated clockwise, and to curve in another direction when rotated counter-clockwise. In one embodiment, described in detail below, knob 151 can be attached to two steering wires which are captured in the distal portion and cause bi-directional steering such as symmetric or asymmetric steering. In alternative embodiments, 1, 3, 4 or more steering wires may be incorporated, such as steering wires separated by 120° or 90°, causing deflection in a single plane, or three or more planes. Each deflection may have a simple geometry such as a single plane, fixed radius curve, or more complex geometries.

Additional controls may be integrated into handle 150 to perform additional functions. A connector, not shown, can be integral to handle 150 and allows electrical connection of ablation catheter 100 to one or more separate devices such as an RF generator or other energy delivery unit; a temperature monitoring system, an ECG monitoring system; a cooling source; an inflation source, and/or numerous other electromechanical devices.

A distal portion of the shaft can include shaft ablation assembly 120 having multiple ablation elements, such as ablation elements 121*a*, 121*b*, 121*c* and 121*d*. The shaft can further include distal ablation assembly 130, which preferably includes at least one ablation element, such as an atraumatic (e.g. rounded tip), platinum, tip electrode configured to deliver RF energy to tissue. In a preferred configuration, ablation elements 121*a*, 121*b*, 121*c* and 121*d* are platinum electrodes configured to deliver unipolar energy (energy delivered between that electrode and a return pad), and/or bipolar energy (energy delivered between that electrode an a second electrode in general proximity to the first electrode). Distal ablation assembly 130 may include multiple ablation elements, such as multiple platinum electrodes separated by an insulator, and/or deployable from the distal end of shaft 110 (e.g. via a control on handle 150). Distal ablation assembly 130 and shaft ablation assembly 120 can further include one or more temperature sensors (not shown), such as at least one thermocouple mounted to each ablation element. The temperature sensors can also be integrally formed with the distal and shaft ablation assemblies.

In one embodiment, the ablation elements of catheter 100 can be electrodes attached to signal wires traveling within shaft 110 and electrically connecting to an electrical connector on handle 150. The signal wires, described in detail in reference to subsequent figures, can carry power to the electrodes for unipolar and/or bipolar energy delivery, and also can receive signals from the electrodes, such as ECG mapping signals of the human heart. The signal wires can also transmit or receive information from one or more other functional elements of catheter 100, such as a sensor (e.g., a thermocouple), or a transducer (e.g., an ultrasound crystal).

In one configuration, two signal wires of approximately 36 gauge can be connected to a tip electrode of distal ablation assembly 130. The two 36 gauge wires can each simultaneously deliver unipolar energy to the tip electrode, such as up to 45 watts of unipolar energy (approximately 45 Watts being a preferred maximum energy delivery for a tip electrode of the present invention). Minimizing of the diameter of the signal wires provides numerous advantages, such as minimizing the required diameter of shaft 110 as well as preventing undesired stiffening of shaft 110. In an alternative embodiment, one or both of the 36 gauge wires can be configured to prevent embolization of the tip electrode, such as when the joint between the tip electrode and shaft 110 fails. One or both of these signal wires can be attached to a temperature sensor such as a thermocouple and transmit temperature information back to an electrical connector of handle 150, as described above.

In one configuration, a signal wire of approximately 36 gauge and a signal wire of approximately 40 gauge are connected to a shaft electrode such as shaft ablation element 121*a*, 121*b*, 121*c* or 121*d*. Bipolar or unipolar energy can be delivered through the 36 gauge wire, such as a power up to 20 watts (approximately 20 Watts being a preferred maximum energy delivery for a shaft electrode of the present invention). Minimizing of the diameter of the signal wires provides numerous advantages such as minimizing the required diameter of shaft 110 as well as preventing undesired stiffening of shaft 110. One or both of these signal wires can be attached to a temperature sensor such as a thermocouple and transmit temperature information back to an electrical connector of handle 150.

Figure 1A:
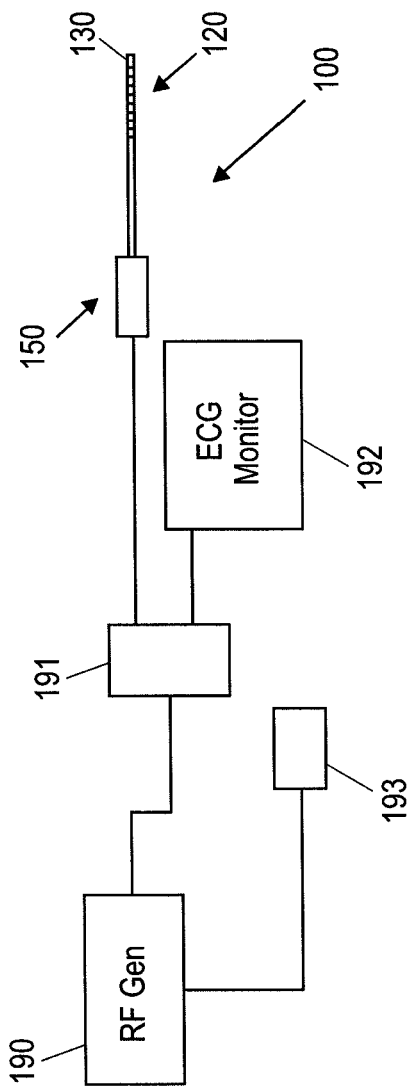
FIG. 1A illustrates a schematic view of an ablation system, consistent with the present invention.

Referring now to FIG. 1A, a preferred embodiment of an ablation system of the present invention is illustrated. System 10 can include an ablation catheter 100 and an energy delivery system, such as RF generator 190. Ablation catheter 100 can be attached to ECG interface 191, such as at handle 150, which in turn can be attached to RF generator 190. RF generator is preferably an RF generator configured to deliver unipolar and bipolar RF energy to the ablation elements of ablation catheter 100. ECG Interface 191 can also be attached to ECG monitor 192 such that the high power energy delivered to ablation catheter 100 by RF generator 190 is isolated from ECG monitor 192. RF generator 190 can be connected to a power source (such as an electrical outlet connected to 110 or 220 AC volts) and can be configured to deliver unipolar and bipolar RF energy to one or more electrodes on distal ablation assembly 130 and shaft ablation assembly 120. RF generator 190 can also be attached to a return pad or ground electrode, such as patient return electrode 193, which is configured to receive the unipolar energy delivered to one or more ablation elements of catheter 100.

Alternatively or additionally, RF generator 190 may deliver other forms of energy, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

In one embodiment, RF generator 190 can provide ablation energy to one or more ablation elements of catheter 100 by sending power to one or more independently controlled RF outputs of RF generator 190. The independent control of each RF output can allow a unique, programmable power delivery signal to be sent to each electrode of ablation catheter 100.

The independent control of each RF output can further allow unique (independent) closed loop power delivery, such as power delivery regulated by tissue temperature (e.g. regulated to tissue temperature of 60° C.) information received from one or more temperature sensors integral to the attached ablation catheter and/or from sensors included in a separate device.

The number of RF outputs can vary as required by the design of the attached ablation catheter. In one embodiment, four to twelve independent RF outputs are provided, such as when the system of the present invention includes a kit of ablation catheters including at least one catheter having from four to twelve electrodes. In another embodiment, sixteen or more independent RF outputs are provided, such as when the system of the present invention includes a kit of ablation catheters including at least one catheter with sixteen or more electrodes.

Unipolar delivery can be accomplished by delivering currents that travel from an RF output of RF generator 190 to an electrically attached electrode of ablation catheter 100, through tissue to return pad 193, and back to RF generator 190 to which return pad 193 has been connected. Bipolar delivery can be accomplished by delivering current between a first RF output which has been electrically connected to a first electrode of an ablation catheter and a second RF output which has been electrically connected to a second electrode of the ablation catheter, the current traveling through the tissue between and proximate the first and second electrodes. Additionally, a combo mode energy delivery can include delivery of both bipolar energy and unipolar energy simultaneously. Combo mode energy delivery can be accomplished by combining the unipolar and bipolar currents described immediately above. The user (e.g. a clinician or clinician's assistant) may select or deselect RF outputs receiving energy to customize therapeutic delivery to an individual patient's needs.

In another embodiment, five different pre-set energy delivery options can be provided to the user: unipolar-only, bipolar-only, and 4:1, 2:1 and 1:1 bipolar/unipolar ratios. A bipolar-only option provides the shallowest depth lesion, followed by 4:1, then 2:1, then 1:1 and then unipolar-only which provides the deepest depth lesion. The ability to precisely control lesion depth increases the safety of the system and increases procedure success rates as target tissue can be ablated near or over important structures. In an alternative embodiment, currents can be delivered in either unipolar mode or bipolar mode only. The preferred embodiment, which avoids bipolar-only, has been shown to provide numerous benefits including reduction of electrical noise generated by switching off the return pad circuit (e.g. to create bipolar-only mode).

In another embodiment, RF generator 190 can include multiple independent PID control loops that utilize measured tissue temperature information to regulate (i.e. provide closed loop) energy delivered to an ablation catheter's electrodes. In one embodiment, RF generator 190 can include twelve separate, electrically-isolated temperature sensor inputs. Each temperature input can be configured to receive temperature information such as from a sensor (e.g., a thermocouple). The number of temperature inputs can vary as required by the design. In one embodiment, four to twelve independent inputs can be provided, such as when the system of the present invention includes a kit of ablation catheters including at least one catheter having four to twelve thermocouples. In another embodiment, sixteen or more independent temperature inputs can be provided, such as when the system of the present invention includes a kit of ablation catheters having at least one catheter with sixteen or more thermocouples.

Ablation target temperatures can be user-selectable and automatically achieved and maintained throughout lesion creation, regardless of blood flow conditions and/or electrode contact scenarios. Temperature target information can be entered via a user interface of RF generator 190. The user interface can be configured to allow an operator to input system parameter information including but not limited to: electrode selection; power delivery settings, targets and other power delivery parameters; and other information. The user interface can be further configured to provide information to the operator, such as visual and audible information including but not limited to: electrode selection, power delivery parameters and other information. Automatic temperature-controlled lesion creation provides safety and consistency in lesion formation. Typical target temperature values made available to the operator range from 50 to 70° C.

In one embodiment, a kit of the present invention includes a first catheter with asymmetric two-way deflection geometries and a second catheter with symmetric two-way deflection geometries. Additional ablation catheters may be included in the system of the present invention, such as ablation catheters configured to: create linear lesions; create lesions proximate pulmonary vein ostia; create lesions on the septum between the left and right atrium; ablation catheters which include multiple carrier arms each with at least one electrode; other ablation catheters; and combinations of these.

Figure 2:
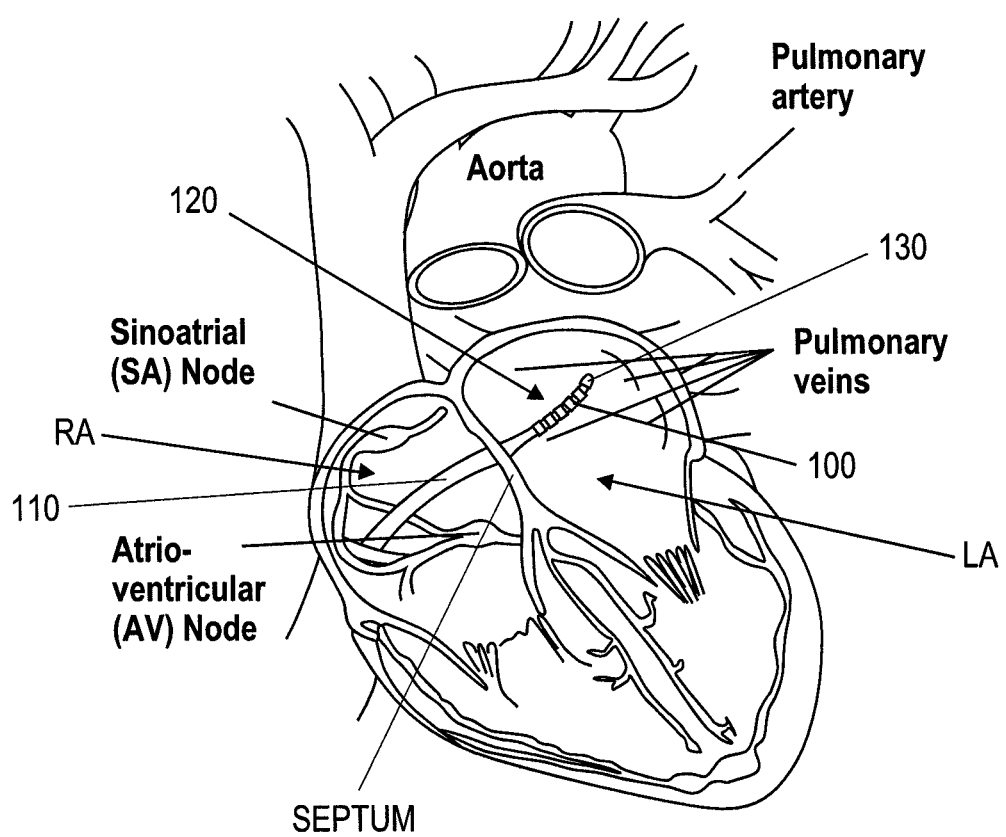
FIG. 2 illustrates an anatomical view of an ablation catheter placed into the left atrium of a heart, consistent with the present invention.

Referring now to FIG. 2, a method of the present invention is illustrated. For the purposes of FIG. 2, it is generally noted that all designs shown may include multiple electrodes, and in preferred configurations may also include a return pad (a large surface area electrode often attached to the patient's back). At least one pair of electrodes, and often many pairs, may be activated or powered with appropriately-powered potential differences to create RF waves that penetrate and ablate desired tissue. If the powering occurs between a pair of electrodes, it is termed "bipolar". If the powering occurs between one electrode and the return pad, it is termed "unipolar". If both bipolar and unipolar power is delivered simultaneously to tissue, it is termed "combo" or "combo mode".

The cross-section of the human heart depicts the atrioventricular node AV and the sinoatrial node SA of the right atrium RA, the pulmonary vein ostia of the left atrium LA, and the septum with the right atrium RA and the left atrium LA. Catheter 100 is shown entering the right atrium RA, passing through the septum, and terminating in left atrium LA. The distal portion of shaft 110 includes shaft ablation assembly 120 and distal ablation assembly 130 as shown in FIG. 2. Distal ablation assembly 130 preferably includes a platinum electrode at its tip. Shaft ablation assembly 120 preferably includes two to six (or more) platinum electrodes secured to the outer diameter of shaft 110. The electrodes of distal ablation assembly 130 and shaft ablation assembly 120 may be configured to deliver unipolar and bipolar RF energy to the heart tissue, such as the tissue of the left atrium LA.

Catheter 100, provided in a sterile form such as via e-beam sterilization and sterile packaging, can be percutaneously inserted in either femoral vein, advanced toward the heart through the inferior vena cava (IVC), and into the right atrium. Through the use of a previously placed transseptal sheath (e.g. a deflectable or fixed shape 9.5 Fr sheath), catheter 100 may be advanced through the septum into the left atrium LA to perform a left atrial ablation. In an alternative embodiment, catheter 100 may be advanced only into the right atrium RA to perform an ablation procedure in the right atrium RA or coronary sinus.

In another method, ablation catheter 100 can be configured to treat paroxysmal atrial ablation and/or chronic atrial ablation. In these procedures, catheter 100 can be used as a reference catheter configured to map electrical activity in the coronary sinus. Alternatively or additionally, ablation catheter 100 may perform an ablation in the right atrium RA or left atrium LA, such as an ablation of: the fasicals proximate the pulmonary veins; the mitral isthmus; and other right atrial RA and left atrial LA locations. In one embodiment, ablation catheter 100 can be configured to be transformed into multiple deflection geometries such that the left and/or right atria can be treated utilizing one or more of these multiple deflection geometries. For example, the ablation catheter can be controlled to assume a first deflection radius (e.g. a radius less than or equal to 28 mm) to ablate a first tissue region, such as the "roof" of the left atrium, tissue proximate the septum, and/or tissue close to the posterior wall. The ablation catheter can then be controlled to assume a second deflection radius to ablate a second tissue region, such as the floor of the left atrium, for example. The second deflection radius can be smaller or larger than the first deflection radius (e.g. less than or greater than 28 mm).

In another method, a small deflection radius can be used to treat atria with a relatively small volume, and a larger deflection radius can be used to treat larger atria (e.g. an enlarged atria of a chronic AF patient). In yet another preferred method, an ablation catheter can be configured to treat the right atrium with a first deflection geometry and the left atrium with a second deflection geometry different than the first deflection geometry. Differences in deflection geometry may include different radius of curvature, such as a first radius of curvature less than or equal to 28 mm and a second radius of curvature greater than or equal to 28 mm.

Ablation catheter 100 may include a handle with a rotating knob. The rotating knob may be operably connected to one or more steering wires such that rotation of the knob in a first direction causes the first radius to be formed and rotating the knob in an opposite direction causes the second radius to be formed.

In another method, ablation catheter 100 may be used to treat atrial flutter. The ablation procedure may be completed with as little as one or two catheter placements allowing the operator to block the aberrant signals causing the flutter. In one method, ablation catheter 100 blocks the aberrant signals with less than 5 placements, preferably less than 3 placements. In another preferred method, the ablation procedure results in bi-directional block. Ablation catheter 100 may be used to treat atrial flutter by creating a lesion along the length of the isthmus, such as with a single ablation. Alternatively or additionally, a lesion may be created proximate the tricuspid annulus, a location known to often include aberrant electrical signals associated with atrial flutter. In another embodiment, ablation catheter 100 can include a deflectable portion which can be deflected in a first direction with a first radius of curvature, and in a second direction with a second, larger radius of curvature. The smaller first radius of curvature can be used to ablate the concave portion of the isthmus, and the larger second radius of curvature can be used to create one or more lesions in the tissue proximate the tricuspid annulus. In one embodiment, the smaller radius of curvature can be at or below 28 mm and the larger radius of curvature can be at or above 28 mm.

Alternatively or additionally, ablation catheter 100 may be used in other methods to treat atrial flutter. In one embodiment, in a first step, the distal portion of ablation catheter 100 can be placed relatively perpendicular to the isthmus, such as with the middle portion of the shaft ablation assembly at a point along the isthmus; in a second step pacing energy can be applied by one or more tip ablation elements while electrograms are recorded by one or more shaft ablation elements; and in a third step pacing energy can be applied by one or more shaft ablation elements while electro grams are recorded by one or more tip ablation elements. Steps 2 and 3 may be repeated until desired electrograms are recorded. In an alternative embodiment, step 3 is performed before step 2. Alternatively or additionally, shaft ablation assembly 120 can include multiple ablation elements, such as multiple electrodes configured to both deliver RF energy and record electro grams. One electrode can be most proximate the proximal end of ablation catheter 100, and one or more electrodes ("middle electrodes") can be located between this most proximate electrode and the distal ablation assembly 130. These one or more middle electrodes can be used to measure "split potential" electro grams, such as electro grams used to confirm adequate block has been achieved. These middle electrodes can be used to identify tissue needing further ablation.

Alternatively or additionally, ablation catheter 100 may be used in yet other methods to treat atrial flutter. In one embodiment, in a first step, the distal portion of ablation catheter 100 can be deflected 90° or more, such as a deflection of 135° or more (deflections not shown for ease of illustration). The one or more ablation elements of shaft ablation assembly 120 and/or distal ablation assembly 130 can be used to deliver ablation energy to tissue proximate the eustachian ridge and/or valley. In one embodiment, ablation catheter 100 includes a deflection mechanism (as described in various embodiments below), and the 90° or more deflection can be accomplished by an operator activating the deflection mechanism, such as via a control on a handle 150 of ablation catheter 100 (handle and control not shown but described in detail in reference to various embodiments herein). Alternatively or additionally, the 90° or more deflection can be accomplished by pressing the distal portion of ablation catheter 100 against tissue, such as tissue proximate the eustachian ridge and/or valley.

Ablation catheter 100 may be used in various ablation procedures in the right atrium RA of the heart. In a preferred method, a lesion can be created between one or more of: the superior vena cava (SVC) and the inferior vena cava (IV C); the coronary sinus (CS) and the IVC; and the SVC and the IVC. In one embodiment, a lesion can be created between all three locations described immediately above. In another right atrial method, ablation catheter 100 can be used to treat sinus node tachycardia by measuring electro grams in tissue proximate the sinus node and ablating tissue proximate the sinus node.

Ablation catheter 100 may be used to ablate tissue proximate or within the coronary sinus (CS). In a preferred method, ablation catheter 100 can deliver bipolar RD energy, such as to improve the treatment of atrial fibrillation (e.g. improving acute and/or chronic results of AF therapy).

Ablation catheter 100 may also be used to treat ventricular tachycardia. In one method, the distal portion of ablation catheter 100 can be placed in the right or left ventricle, and pacing energy can be delivered by one or more ablation elements, such as electrodes, to induce ventricle tachycardia. Information received or determined by the pacing step can be used by an operator to deliver ablation energy to the ventricle with one or more ablation elements of ablation catheter 100. The information may be used to selectively ablate tissue, such as to determine ablation location(s), ablation settings, or another ablation parameter.

The ablation catheter 100 of the present invention is preferably configured to create linear or segmented linear lesions in tissue of a patient, such as heart tissue. The catheter may be further configured to ablate tissue in an arrhythmia treating procedure such as a procedure to treat AF. Ablation catheter may be used in combination with other ablation catheters, such as catheters configured to be used prior to ablation catheter 100 and/or catheters configured to create longer or otherwise larger lesions in tissue such as the left atrium LA. In this subsequent use, ablation catheter 100 may be configured to create smaller lesions that complete a set of lesions to treat AF. These smaller lesions are often referred to as "touch up" lesions.

Ablation catheter 100 and the other ablation catheters of the present invention may be configured to ablate tissue and also map electrical activity in tissue, such as intracardiac electrogram activity. Mapping of AF in humans has shown that areas of complex fractionated atrial electro grams (CFAEs) correlate with areas of slowed conduction and pivot points of reentrant wavelets. Ablation catheter 100, or a system of multiple ablation catheters which include ablation catheter 100, may be used to both identify the areas with AF wavelets reenter, as well as selectively ablate these areas causing wavelet reentry to stop and prevent the perpetuation of AF. Mapping may be performed by one or more ablation elements of ablation catheter 100, such as ablation elements comprising electrodes configured to deliver RF energy. In an alternative embodiment, one or more ablation elements of catheter 100 are further configured to deliver pacing energy, such as electrical energy configured to pace one or more portions of a human heart.

Referring now to FIGS. 3A and 3B, an ablation catheter of the present invention is illustrated. In FIG. 3A, a side-view of a distal portion of catheter shaft 110 is shown. A proximal section 110a can have a larger diameter (e.g. 9 Fr) than a distal section 110b (e.g. 7 Fr). In addition, the proximal section can be stiffer (e.g. by using stiffer material such as 7233 durometer Pebax) than the distal section (e.g. Pebax of 3533 durometer). Shaft 110 is preferably made of one or more biocompatible materials commonly used in catheter construction, such that shaft 110 can be percutaneously introduced to the heart or other location within the body of a patient. Shaft 110 may be a laminate construction, such as a structure including: braiding such as stainless steel braid; embedded or attached members such as stiffeners and malleable (plastically deformable) members; liners such as Teflon liners which provide a low-friction surface for sliding members within shaft 110; and elongate tubes which reside within shaft 110.

As shown, the proximal section of the catheter shaft can transition from a larger size (e.g., 9 Fr) to a smaller size (e.g., 7 Fr) at tapered joint 113. In a preferred manufacturing method, a larger (e.g., 9 Fr tube), a smaller (e.g., 7 Fr tube), and a tapered tube which tapers from the larger size to the smaller size are bonded together, such as via heat bonding, adhesive bonding, or a combination of the two.

Also shown in FIG. 3A is a "staircase joint" 112 joining the proximal and distal sections, in which shaft 110 tapers or transitions from a stiffer material (e.g. 7233 durometer Pebax) to a more flexible material (e.g. 3533 durometer Pebax). Staircase joint 112 can include an overlap of the stiffer material with the more flexible material, such as with the two materials overlapping each other as shown in FIG. 3A. Staircase joint 112 may be constructed by cutting the step profile into two tubes of different stiffness and thermally bonding the two steps together. Alternatively or additionally, adhesive may be used. Staircase joint 112 provides a "hinge point" for deflection (steering), such as a deflection caused by advancement and/or retraction of a steering wire, not shown but described in detail in reference to subsequent figures below. Staircase joint 112 may include an inserted elongate member, such as an elastically biased member of Nitinol wire or stainless steel wire, or a malleable member. Steering of shaft 110 is typically 90° or more. Joint 112 can avoid the need for creating a hinge point with a collar in the wall of and/or within a lumen of shaft 110. Joint 112 can also be configured such that deflection toward the stiffer material (i.e. towards the top of the page in FIG. 3A), is less (e.g. less curvature and greater radius of curve) than the deflection toward the more flexible material (i.e. towards—the bottom of the page in FIG. 3B). Numerous other geometries of joints which joint two dissimilar materials arranged to cause asymmetric deflection geometries may be incorporated, such as tapered joint 112' of FIG. 3C which includes a continuous taper between the two materials, and joint 112" of FIG. 3D which includes a "toothed" joint construction.

The catheter shaft of FIG. 3A can be constructed in numerous shapes and sizes. In one preferred embodiment, the distance from joint 112 to the distal tip of the shaft can be approximately 2", the size of joint 112 can be approximately 0.7", the distance from the distal end of taper 113 to joint 112 can be approximately 1", and the size of taper 113 can be approximately 0.2", for example.

Alternatively or additionally, shaft 110 may be modified with a stiffening member, not shown but located within the wall of or attached proximate an inner or outer wall of shaft 110, such as to create asymmetric deflection during steering and/or to provide a restoring force (e.g. a force configured to straighten or curve the distal portion of shaft 110). The stiffening member may be maintained proximate to shaft 110 with a braid or a liner. In one embodiment, an elastic stiffener can be attached to one side of shaft 110, such that deflection toward that side is less than deflection toward the opposite site. In another embodiment, a plastically deformable stiffener can be similarly attached, such that one or more curved shaped can be maintained until a restoring force is applied. Alternatively or additionally, shaft 110 may include an eccentric braid (absent or reduced in a portion of the full inner diameter of shaft 110), such that deflection toward the stiffer part of the braid is less than deflection toward the less stiff braid portion.

Referring back to FIG. 3A, an ablation element, such as tip electrode 131, can be positioned the distal end of shaft 110. Tip electrode 131 is preferably made of platinum and designed to have an atraumatic leading edge (such as to prevent perforation of the left atrium or other sensitive heart tissue). Tip electrode 131 can be adhesively bonded to shaft 110, and may further include a reduction of (including a portion of) its internal diameter such as via a crimp or swage on its proximal end to increase the attachment force to shaft 110. In an alternative embodiment, tip electrode 131 and the distal end of shaft 110 may have reverse, mating tapers (e.g., a "Chinese finger grip") such that an applied tension force causes increased attachment force. A crimp, swage or other geometry modification can also perform the function of removing a sharp edge on a tip (or shaft) electrode. Tip electrode 131 preferably has a length of 1 to 8 mm, and more preferably has a length of approximately 4 mm. Tip electrode 131 preferably has an inner diameter of 0.020" to 0.300" and more preferably has an inner diameter of approximately 0.094". Tip electrode 131 typically has a surface area of approximately 33.7 $mm^2$, and preferably has a wall thickness of between 0.006" and 0.010", typically between 0.008" and 0.010". In an alternative embodiment, tip electrode 131 has a wall thickness between 0.002" and 0.020".

Proximal to tip electrode 131 can be a series of electrodes such as shaft electrodes 121. In a preferred embodiment, 2 to 6 shaft electrodes are included. In an alternative embodiment, a single shaft electrode is attached to shaft 110. Shaft electrodes 121 have an inner diameter configured to allow adhesive attachment of electrodes 121 to shaft 110 (e.g. closely matched diameters). In one embodiment, one or both of the ends of electrodes 121 are swaged or crimped to increase the attachment force to shaft 110. The outer diameter of shaft electrodes 121 may be sized to be flush with the outer diameter of shaft 110, or in another embodiment, the outer diameter of shaft electrodes 121 can be slightly larger than the outer diameter of shaft 110 such that increased engagement with tissue can be achieved. In an alternative embodiment, shaft 110 includes a recessed portion on its outer diameter where shaft electrodes 121 can be attached. Shaft electrodes 121 preferably have a length of 1 to 8 mm, and more preferably have a length of approximately 2 mm. Shaft electrodes 121 preferably have a diameter of 0.020" to 0.300" and more preferably have a diameter of approximately 0.094" (e.g. when shaft 110 has a diameter of 0.090"). Shaft electrodes 121 typically have a surface area of approximately 29.5 mm$^2$, and preferably have a wall thickness of between 0.006" and 0.010", typically between 0.008" and 0.010". The shaft electrodes may also have similar or dissimilar geometries and/or materials of construction. In one embodiment, the shaft electrodes can be of different lengths or different thicknesses.

The shaft electrode 121 closest to tip electrode 131 (i.e., the distal most shaft electrode) can be located approximately 1 to 8 mm from tip electrode 131, and more preferably 3 mm. The separation between shaft electrodes 121 is preferably 1 to 8 mm, and more preferably 3 mm. Each of the ablation elements mounted on shaft 110, is preferably a platinum electrode configured to deliver unipolar energy or bipolar energy (e.g. bipolar energy between adjacent electrodes or any pair of electrodes. Alternatively or additionally, one or more ablation elements may be an electrode constructed of platinum-iridium, gold, or other conductive material. Alternatively or additionally, the ablation elements may deliver another form of energy, including but not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

Shaft electrodes 121 and tip electrode 131 preferably include at least one temperature sensor such as a thermocouple. In one embodiment, each electrode can include at least two thermocouples, such as two thermocouples mounted (e.g. welded) to the inner diameter of each electrode and separated by 180°. In an alternative embodiment, three or more thermocouples can be mounted to the inner diameter of one or more electrodes, such as the thermocouples being mounted at locations equidistant from each other. In another alternative embodiment, two or more thermocouples can be mounted in an eccentric geometry, such as a geometry relating to one or more particular deflection geometries of the shaft (e.g., a first thermocouple located on the outside of the curve of a first deflection geometry and a second thermocouple located on the outside of the curve of a second deflection geometry). In another embodiment, one or more thermocouples can be potted into an electrode wall such that the thermocouple is in direct contact with tissue during ablation. One or all of the thermocouples can be mounted, welded, glued, or attached within holes or openings in the electrode wall. In this particular embodiment, the thermocouple(s) can be flush with or reach beyond the outer diameter of the electrodes and extend through the openings in the electrodes into the catheter shaft. Signal wires, not shown, attach to the electrodes as well as the thermocouples, for delivering energy to the electrodes as well as transmitting information signals (e.g. temperature levels) back to the handle of the ablation catheter to which shaft 110 is attached.

Referring now to FIG. 3B, a partial cross-section of catheter shaft 110 of FIG. 3A is shown. In order to generate the asymmetric deflection described in reference to FIG. 3A (noting that staircase joint 112 is not shown), two steering wires 115 are included within the shaft 110. In the larger diameter portion (e.g. 9 Fr portion), steering wires 115 "free float" within a lumen of shaft 110. At a point distal to tapered joint 113, the steering wires 115 are fixedly attached to or embedded within shaft 110 (e.g. between a braid and shaft 110 and/or between a liner and shaft 110, braid and liner not shown but described in detail in description of subsequent figures herebelow). This configuration of the steering wires 115 results in one or more improvements including but not limited to: creation of a strain relief such as when shaft 110 is in tension (versus securing with a anchoring band which may create an undesired failure point during tensile loading); an increase in torque response of the distal portion of shaft 110; reduced "whipping" (undesired rotations or other undesired movement of a distal portion of a catheter while the proximal end of the catheter is applied with a torsional force); reduced "snaking" (deflection of an undesired, long portion of a catheter shaft, including deflection of the entire shaft); and combinations of these.

Also shown in FIG. 3B is tip electrode 131 and shaft electrodes 121. In addition to adhesive applied to the inner diameter of each electrode, and crimping, swaging or otherwise modifying of one or more ends, a fillet material, fillet 132 for tip electrode 131 and fillet 122 for shaft electrodes 121 may be included. Fillet material is preferably an adhesive, configured to further secure each electrode as well as eliminate a sharp edge at each electrode end.

Alternatively, the fillet material may be a polymer, such as the Pebax shaft material, the fillet formed by adding Pebax and/or reflowing Pebax material with heat.

Figure 4:
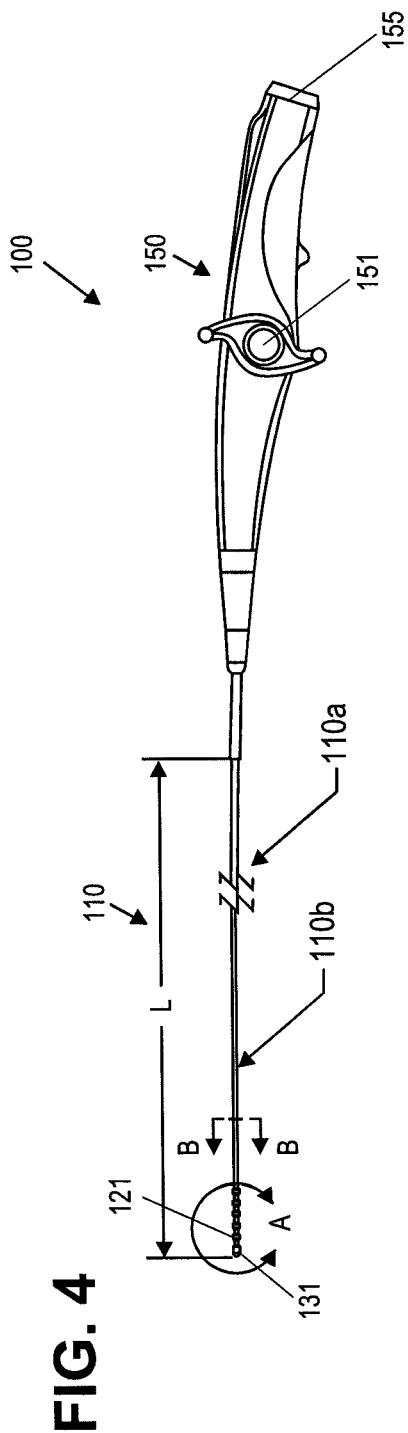
FIG. 4 illustrates a side view of an ablation catheter, consistent with the present invention.
Figure 4A:
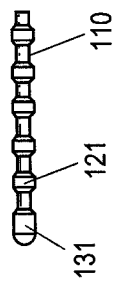
FIG. 4A illustrates a side view of the distal end of the ablation catheter of FIG. 4.
Figure 4B:
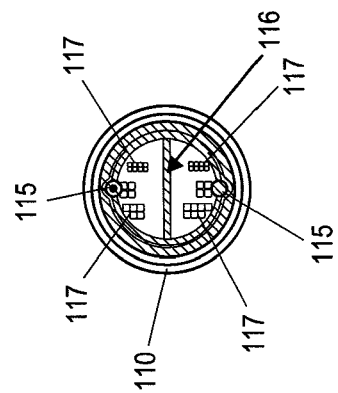
FIG. 4B illustrated a cross sectional view of the shaft of the ablation catheter of FIG. 4.
Figure 4C:
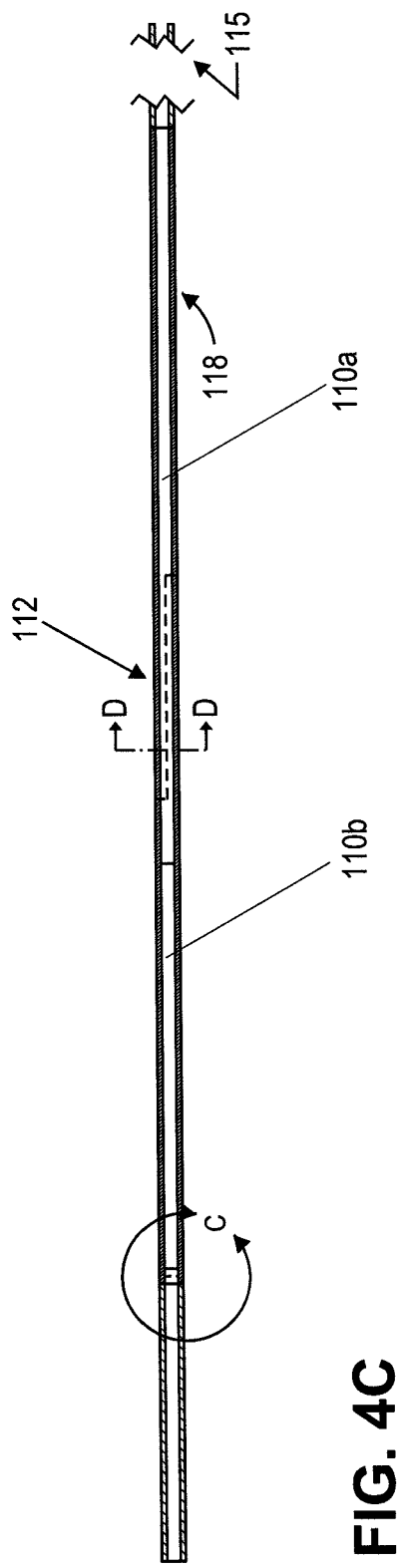
FIG. 4C illustrates a side view of a preferred construction of a shaft subassembly of the catheter of FIG. 4.
Figure 4E:
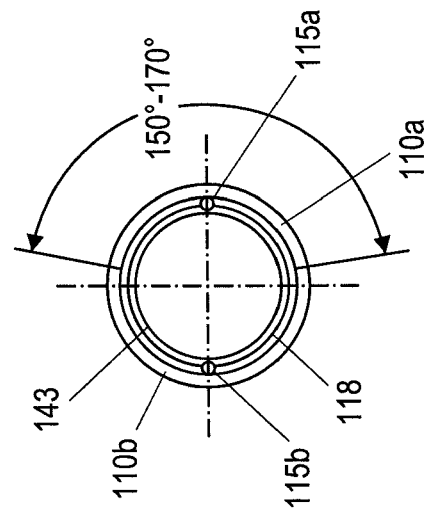
FIG. 4E illustrates a cross sectional view of the catheter shaft subassembly of FIG. 4C.

Referring now to FIGS. 4-4E, another embodiment of an ablation catheter is illustrated. In FIG. 4, a side-view of ablation catheter 100 is shown. The total length L of the catheter shaft can be approximately 105 cm±5 cm, for example. Shaft 110 can include a larger diameter proximal section 110a and a smaller diameter distal section 110b, both of which are preferably braided. Alternative shaft reductions may be employed, such as an tapered transition, or other transitions preferably including a reduction of approximately 2 Fr. Braiding comprises typically a stainless steel flat wire and/or a nylon strand braiding material, although a wide variety of materials and cross-sectional geometries can be used for braiding. The stainless steel flat wire is typically 0.001"× 0.003" type 304 stainless steel, or equivalent. Braiding parameters preferably range from 40 ppi to 80 ppi. In another preferred embodiment, braiding of 80 ppi in the proximal portion of shaft 110 transitions to 60 ppi and then 40 ppi in the distal portion, such as to create a relatively constant torque transition during rotation.

Ablation catheter 100 can include handle 150 having an electrical connector, jack 155, which is electrically connected via multiple signal wires (not shown) to shaft electrodes 121 and tip electrode 131. Handle 150 can further include knob 151, which is operably attached to one or more steering wires, also not shown but described in detail throughout this application. Rotation of knob 151 can cause deflection of the distal portion of shaft 110, such as deflections in one to four directions, with symmetric and/or asymmetric deflection geometries. Alternative or additional knobs may be included, such as a knob attached to a control wire which is further attached to a stiffening member, such as a stiffening member used to change the curve of a distal portion of shaft 110.

In FIG. 4A, a side view of the distal end of shaft 110 is illustrated (detail A of FIG. 4), including shaft electrodes 121 and tip electrodes 131. While the separations between each electrode are shown as relatively similar, dissimilar separation distances may be employed. While the lengths of shaft electrodes 121 are shown as relatively similar, dissimilar electrode lengths may be employed.

In FIG. 4B, a cross sectional view of shaft 110 is illustrated (cross section B-B of FIG. 4). Included within shaft 110 is guide plate 116, an elongate plate constructed of an elastic material such as stainless steel or Nitinol. Steering wires 115 are also shown, located approximately 180° from each other and fixedly attached or embedded to shaft 110. The axis formed between the centers of each steering wire 115 is perpendicular to the longer axis of guide plate 116. In this construction, deflections in the plane of guide plate 116 are resisted (i.e. guide plate 116 has a preferred bending direction due to the high aspect ratio of its width versus height). Guide plate 116 further improves lateral stiffness of shaft 110. Guide plate 116 can be fixedly attached (e.g. adhesive attachment) within shaft 110 near its distal end (within or near tip electrode 131) and travels proximally 1" to 8", preferably 5" and also preferably to a location more proximal than the transition between the smaller diameter and larger diameter sections of the shaft. Guide plate 116 is preferably not attached to any steering wire or steering mechanism.

Also shown in FIG. 4B are multiple signal wires 117, shown grouped in multiple bundles, which transmit energy, such as RF energy, to the ablation elements of catheter 100 such as tip electrode 131 and shaft electrodes 121. Signal wires 117 can also receive signals from one or more sensors, such as pairs of thermocouples mounted to or integral with each electrode. Signal wire sizes and function are described in detail throughout this application, and specifically in reference to FIG. 1. In one embodiment, tip electrode 131 can be attached to two 36 gauge wires and shaft electrodes 121 are each attached to a 36 gauge wire and a 40 gauge wire. Tip electrode 131 can be configured to deliver up to 45 Watts of RF power utilizing the two 36 gauge wires. Shaft electrode 121 can be configured to deliver up to 20 watts of RF power, utilizing the one 36 gauge wire.

In FIG. 4C, a side view of a preferred sub-assembly of shaft 110 is illustrated. The distal end of the shaft can be trimmed in manufacturing, and the tip electrode is attached. The subassembly of shaft 110 includes shaft proximal section 110a, preferably Pebax at 5533 to 7533 durometer (typically 7533 durometer); and shaft distal section 110b, preferably Pebax at 3533 to 4533 durometer (typically 3533 durometer), or at least of a material more elastic that the material of shaft proximal section 110a. Shaft proximal section 110a is fixedly attached (e.g. via thermal bond) to shaft distal portion 110b at staircase joint 112. The subassembly of shaft 110 can include braid 118, as has been described hereabove.

Figure 4D:
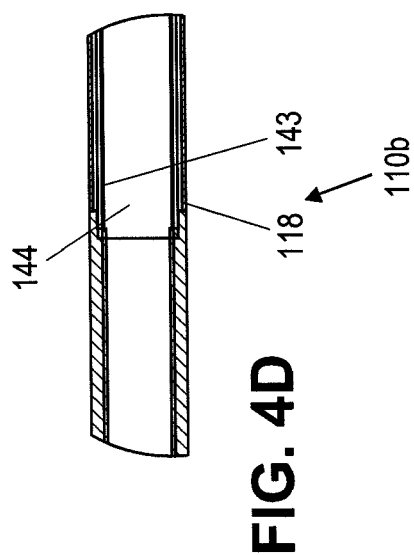
FIG. 4D illustrates a side sectional view of a portion of the shaft subassembly of FIG. 4C.

In FIG. 4D, side sectional view of detail C of FIG. 4C is illustrated. The distal end of shaft distal section 110b is constructed of stiffer material than the more proximal portion distal section 110b (e.g., 5533 durometer versus 3533 durometer). The majority of the stiffer portion is trimmed in manufacturing, however a small amount remains which is later fixedly attached to tip electrode 131. The increased durometer provides a more stable platform for an adhesive bond, as well as for a mechanical engagement such as a crimp or swage. During manufacturing, a metal ring, anchor ring 144 is placed at the junction of the stiffer portion and the less stiff portion of the distal section 110b of the shaft as shown. Shaft distal section 110b can include liner 118, such as a Teflon liner, which can be placed such that one or more steering wires, not shown, are sandwiched between liner 118 and shaft 110b. In a preferred embodiment, liner 118 can travel proximally into shaft proximal section 110a. Anchor ring 118 can apply additional retaining force to prevent steering wire movement. Anchor ring 118 can span across the differing stiffnesses of distal section 110b.

In FIG. 4E, an end cross sectional view of section D-D of FIG. 4C is illustrated. Section D-D is positioned within staircase joint 112, and indicates a preferred construction where the stiffer shaft proximal section 110a occupies 150° to 170° of the diameter of the shaft, and the more flexible shaft proximal portion 110b occupies 190° to 210° of the diameter. In an alternative embodiment, shaft proximal section 110a occupies 150° to 180° of the diameter of the shaft. The eccentric mating of materials in staircase joint 112 can produce asymmetric, stable deflection geometries. FIG. 4E depicts a laminate construction including liner 143, braid 118 and shaft proximal section 110a and shaft distal section 110b. Positioned between liner 143 and shaft proximal portion 110a is a first steering wire 115a, and positioned between liner 143 and shaft distal portion 110b is a second steering wire 115b. Also included are signal wires, connecting the ablation elements to a jack on a handle mounted to the proximal end of shaft 110, signal wires, ablation elements, handle and jack not shown but described in detail throughout this application.

Figure 5A:
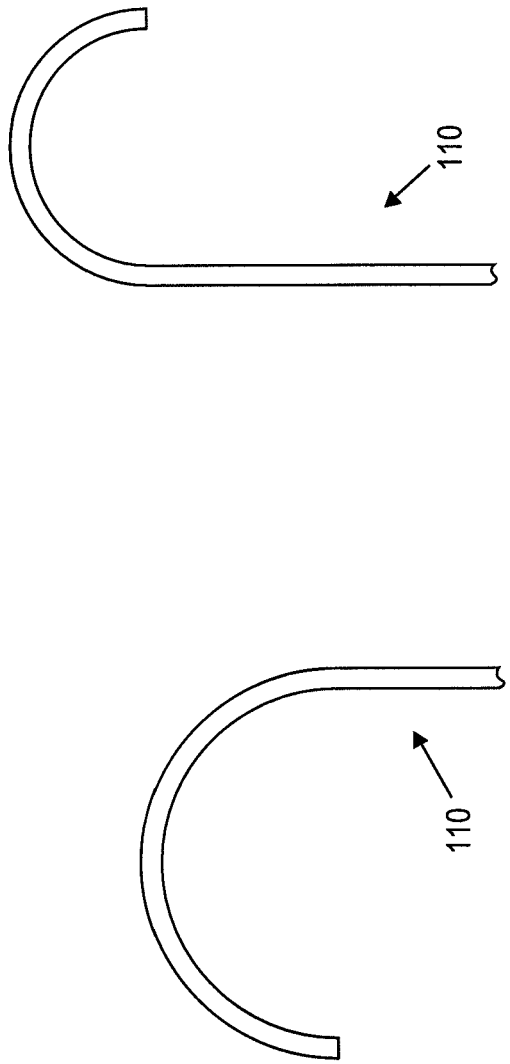
FIG. 5A illustrates a side view of two asymmetric deflection geometries of the distal portion of a single catheter shaft, consistent with the present invention.
Figure 5B:
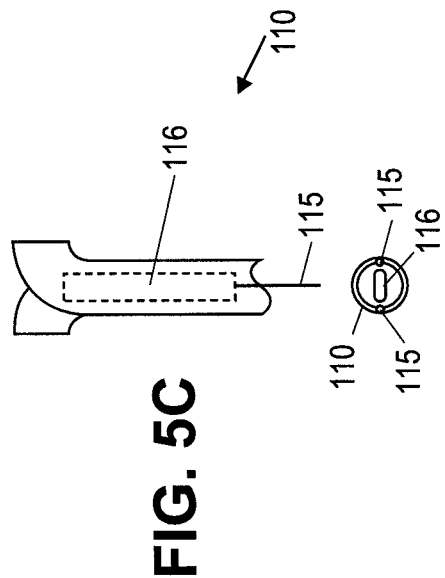
FIGS. 5B and 5C illustrate side and end views of a distal end of a catheter shaft, including a guide plate consistent with the present invention.
Figure 5C:
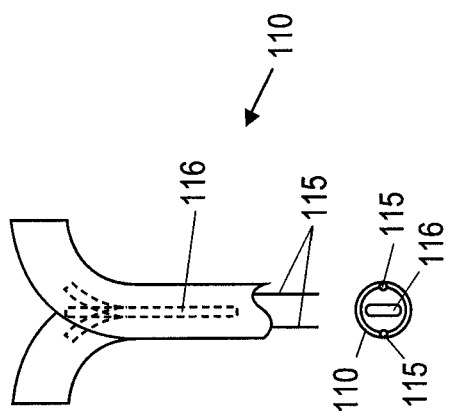

Referring now to FIGS. 5A, 5B and 5C, side views of the end of ablation catheter 100 of FIG. 4 are illustrated. In FIG. 5A, two deflections of the distal end of shaft 110 are shown, depicting typical asymmetric deflections (i.e. larger radius of curvature when deflecting toward the left side of the page). For example, the distal end of the shaft may have a radius of curvature of approximately 0.85" when deflected in one direction (e.g., as illustrated on the left side of FIG. 5A) and may have a radius of curvature of approximately 0.60" when deflected in the opposite direction (e.g., as illustrated on the right side of FIG. 5A). Additionally, the differing radii of curvature may cause the shaft to deflect at different points along the shaft. For example, as shown in FIG. 5A, when deflecting with a larger radius of curvature, the shaft is deflected at a point more proximal to the point of deflection when the shaft is deflected with a smaller radius of curvature. The distance between deflection points can be approximately 0.75", for example. Numerous asymmetric deflection configurations, as are described throughout this application, can be employed to cause this asymmetry. The staircase joint 112 of FIG. 3A and FIG. 4C, the inclusion of a guide plate such as the guide plate of FIG. 4B, the addition of a stiffening member in or near shaft 110 (as is described in reference to FIG. 10 herebelow), non-uniform braiding patterns, and other eccentric constructions may individually, or in combination, create asymmetry between two or more deflection directions.

FIGS. 5B and 5C include side view and cross sectional views of shaft 110 near the deflection point of the shaft. The shaft 110 can include a guide plate 116, configured to limit motion in a plane and/or create asymmetric deflection. FIG. 5B includes an end sectional view and a side view, each showing deflection amounts. In FIG. 5B, the plane of guide plate 116 can be perpendicular to the deflection directions, and deflection is only marginally resisted (by the relatively low stiffness of guide plate 116). In FIG. 5C, the plane of guide plate 116 can be parallel to the deflection directions, and deflection is met with a very large force, limiting the magnitude of the deflection. In alternative embodiments, guide plate 116 can be at an angle between perpendicular and parallel to the deflection direction, creating more complex geometries of deflection (e.g. 3-D geometries). In another alternative embodiment, the guide plate length is selected to determine the geometry of deflection.

Referring now to FIG. 6, an exploded view of a preferred construction of handle 150 of catheter 100 is illustrated. Handle 150 can include multiple controls, such as knobs or buttons which can manipulate the geometry of the catheter (e.g. via steering wires and the symmetric and asymmetric deflection mechanisms described above), activate a functional element mounted to the catheter shaft or tip (e.g. an ablation element consisting of a platinum electrode), and permit, cause, activate or de-activate other functions. Handle 150 can be fixedly attached to shaft 110, which includes distal tip electrode 131 and shaft electrodes 121. Ablation catheter 100 can also include a capture device 300 which can be placed at the junction between handle 150 and shaft 110 and be slidably received by shaft 110. When removably attached to handle 150, capture device 300 can act as a strain relief for shaft 110. Alternatively or additionally, capture device 300 can be slidably moved toward the distal end of catheter 100, engage the proximal side of the distal end and capture the distal end within capture device 300, allowing protected insertion of the distal end of catheter 100 into a percutaneous introducer.

Handle 150 can include a tensioning mechanism such that the force required to perform a deflection can be adjusted and/or a specific deflection geometry can be maintained.

Handle 150 can include the following components as shown: bottom housing 51, preferably of polycarbonate construction; cam 52, preferably of polycarbonate construction; screw 53, preferably of stainless steel construction and configured to adjust a steering parameter; hypotube coupling 54 preferably of stainless steel construction; PC Board assembly 55 configured to perform one or more switching or other functions; connector sleeve 56, connector 57 configured to electrically attach one or more components of ablation catheter 100 to a separate device such as an RF generator or an ECG monitor; top housing 58 preferably of polycarbonate construction; O-Ring 59 preferably of n-buna rubber construction; steering knob 60 preferably of polycarbonate construction; tension adjust knob 61 preferably of polycarbonate construction; tension adjust screw 62; dowel pins 63; tension control knob 64; and handle overmold grip 65.

Referring now to FIGS. 7A and 7B, which illustrate end and side sectional views, respectively, of a preferred construction of a shaft electrode. Shaft electrode 121 is preferably manufactured of platinum or platinum-iridium and configured to deliver unipolar or bipolar RF energy. Shaft electrode 121 can include a wall 136, shown at uniform thickness but alternatively of varied thickness. Preferred dimensions are an inner diameter of 0.093" to 0.095", a wall thickness of 0.006" to 0.010", and a length of 1 to 8 mm, more preferably a length of 2 mm. In a preferred embodiment, the ratio of the outer diameter of shaft electrode 121 to the inner diameter of the shaft electrode is in the range of 1.09:1 to 1.11:1, and more specifically a ratio of approximately 1.10:1. Inner diameter to outer diameter ratios in this range have been shown to produce superior lesions such as lesions created which block aberrant electrical signals but significantly limit the possibility of tissue charring or coagulum formation.

Shaft electrode 121 can include two thermocouples 138a and 138b, although a single thermocouple or three or more thermocouples could be incorporated. Thermocouples 138a and 138b can be located approximately 180° from each other on the inner diameter of shaft electrode 121. Thermocouples 138a and 138b can be placed at the approximate midpoint of (the length of) shaft electrode 121, although other locations can be used such as the proximal and/or distal ends of the electrode. Additional thermocouples may be incorporated creating symmetric or asymmetric thermocouple positioning geometries. When manufactured into an ablation catheter of the present invention, shaft electrode 121 as well as thermocouples 138a and 138b can be electrically attached to signal wires which travel proximally to a handle of the device, as has been described in detail above.

Referring now to FIGS. 7C and 7D, which illustrate end and side sectional views, respectively, of a preferred construction of a tip electrode. Tip electrode 131 is preferably manufactured of platinum or platinum-iridium and configured to deliver unipolar and/or bipolar RF energy. Tip electrode 131 can include a rounded, or otherwise atraumatic distal end. Tip electrode 131 can also include a wall 137, shown at uniform thickness but alternatively of varied thickness, such as a thicker wall in the rounded tip area. Preferred dimensions are an inner diameter of 0.093" to 0.095", a wall thickness of 0.006" to 0.010", and a length of 1 to 8 mm, more preferably a length of 4 mm. In a preferred embodiment, in the straight portion of tip electrode 131, the ratio of the outer diameter to the inner diameter is in the range of 1.09:1 to 1.11:1, and more specifically a ratio of approximately 1.10:1. Inner diameter to outer diameter ratios in this range have been shown to produce superior lesions such as lesions created which block aberrant electrical signals but significantly limit the possibility of tissue charring or coagulum formation.

Tip electrode 131 can include two thermocouples 139a and 139b, although a single thermocouple or three or more thermocouples could be incorporated. Thermocouples 139a and 139b can be located approximately 180° from each other on the inner diameter of tip electrode 131. Thermocouples 139a and 139b are placed at the approximate midpoint of the tip electrode 131, although other locations can be used, such as closer to the distal end of tip electrode 131. Additional thermocouples may be incorporated creating symmetric or asymmetric thermocouple positioning geometries. When manufactured into an ablation catheter of the present invention, tip electrode 131 as well as thermocouples 139a and 139b can be electrically attached to signal wires which travel proximally to a handle of the device, as has been described in detail above.

Referring now to FIG. 7E, a side sectional view of a preferred construction of the distal portion of a shaft of an ablation catheter of the present invention is illustrated. The distal portion of shaft 110 can include at its distal end, tip electrode 131 which can be adhesively mounted to the distal end of shaft 110. In one embodiment, the proximal end of tip electrode 131 can also be crimped or swaged onto shaft 110, and an adhesive fillet 132 can be incorporated, both described in detail above. Shaft 110 can further include guide plate 116, preferably a flat stainless steel plate, with a high ratio of width to thickness and a length that can traverse proximally to a point where shaft 110 changes from a first diameter to a larger second diameter (e.g. approximately 5 inches in length). Guide plate 116 can resist bending in certain directions, as has been described above. A restoring, or straightening force can also be provided by guide plate 116, such that when a deflecting force is removed, guide plate 116 and shaft 110 straighten. In an additional or alternative embodiment, guide plate 116 may have a variable thickness, such as a greater thickness at its distal end than its proximal end, or a greater thickness at its proximal end than its distal end. In one embodiment, one end has a thickness of 0.005" and the other end has a thickness of 0.002". Shaft 110 can include multiple shaft electrodes 131, in a band construction (reference FIGS. 7A and 7B) and adhesively mounted to shaft 110. Adhesive fillets 122 can be included to create a smooth edge and increase the attachment force of shaft electrodes 121. Shaft 110 can further include braid 118 and steering wires 116, as has been described in detail above.

Figure 8A:
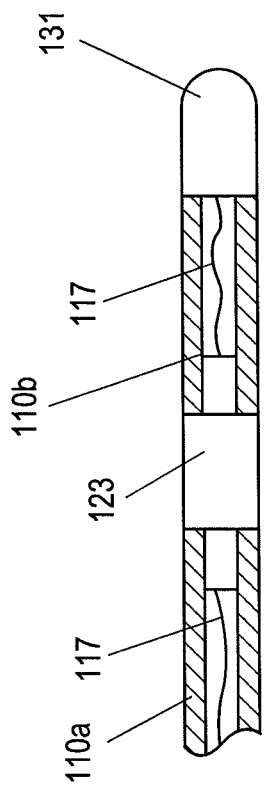
FIG. 8A illustrates a side sectional view of the distal end of a catheter shaft, with an in-line shaft electrode, consistent with the present invention.
Figure 8B:
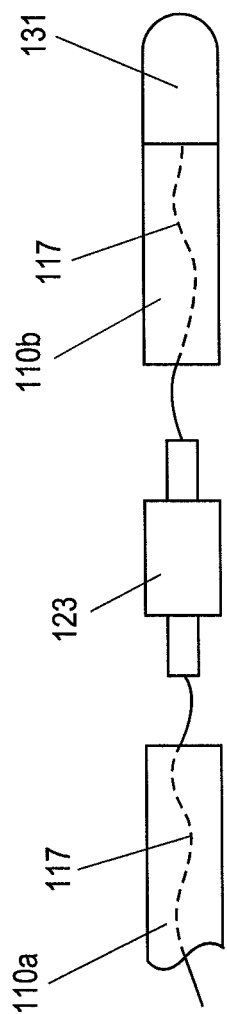
FIG. 8B illustrates an exploded view of FIG. 8A.

Referring now to FIGS. 8A and 8B, an alternative construction of a shaft electrode of the present invention is illustrated. FIG. 8A depicts shaft electrode 123 in an assembled configuration of an ablation catheter, and FIG. 8B shows an exploded view of the construction of FIG. 8A. Shaft electrode 123 can include a reduced diameter flange on each end, sized to approximate the inner diameter of proximal section 110a and distal section 110b. Shaft electrode 123 can include a middle portion with a diameter approximating the outer diameter of shaft 110, preferably a slightly larger diameter (e.g. a diameter 0.001"-0.050" larger, preferably approximately 0.004" larger). Shaft electrode 123 can include one or more thermocouples mounted to its inner surface, not shown but more preferably two thermocouples positioned approximately 180° from each other on the inner diameter of shaft electrode 123. Signal wires 117 pass through a lumen of the shaft and attach to shaft electrode 123. One or more signal wires 117 may pass through a lumen of shaft electrode 123 (lumen not shown), travel distally through a lumen of the shaft, and terminate with a connection to tip electrode 131, which is fixedly attached to the distal end of the shaft. Shaft electrode 123 and tip electrode 131 can be configured to provide ablation energy, record electrical and temperature signals, and perform other functions as has been described above in reference to the ablation elements of the present invention.

Figure 9A:
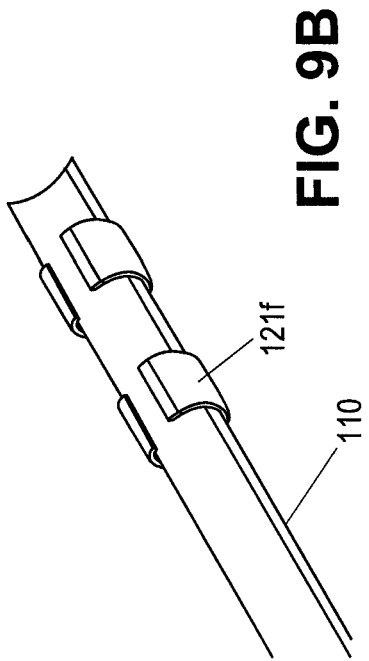
FIG. 9A illustrates a perspective view of a preferred configuration of two shaft electrodes, each with helical geometry, consistent with the present invention.

Referring now to FIGS. 9A through 9O, numerous configurations of ablation elements, particularly shaft electrodes and tip electrodes, of the ablation catheters of the present invention are illustrated. The electrodes may be configured in symmetric or asymmetric geometries. The electrodes may have smooth surfaces on their inner diameter and/or outer diameter, or may include surface modifications such as bumps, ridges, dimples or grooves (such as to increase surface area or modify blood flow), and may include projections such as heat dissipating fins. The electrodes may have relatively uniform wall thicknesses, or the walls may have varied thicknesses such as tapered or stepped profiles. Each of the electrodes is preferably configured to be attached to multiple thermocouples configured to provide redundant temperature information for one or more energy delivery algorithms. Each of the electrodes is preferably made of platinum or platinum-iridium, although any material that can transmit RF energy to tissue can be used. In addition to providing ablative RF energy, each of the ablation elements of the present invention can preferably provide the function of recording electrical signals found in tissue, such as ECG signals.

Referring specifically to FIG. 9A, a perspective view of two helically shaped shaft electrodes is shown. Electrodes 121e' and 121e" are configured to be mounted to a shaft of an ablation catheter of the present invention, such as in a flush or raised mounting scheme. The large surface area of electrodes 121e' and 121e" can provide an enhanced cooling effect. While either electrode could be used singly, use of both electrodes positioned as shown in FIG. 9A would support both unipolar and bipolar (between electrode 121e' and 121e" or to a separate electrode) RF energy delivery. In addition, electrodes 121e' and 121e" could record bipolar electrograms.

Figure 9B:
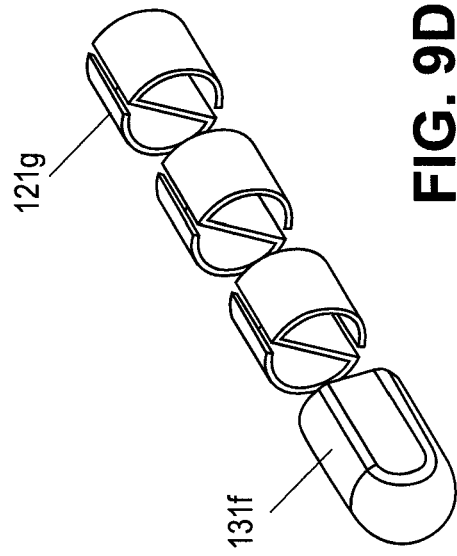
FIG. 9B illustrates a perspective view of a preferred configuration of a shaft electrode, with partial band geometry and fixedly mounted to a catheter shaft, consistent with the present invention.

Referring specifically to FIG. 9B, a perspective view of two partial band shaft electrodes 121f are shown mounted to shaft 110. The partial band construction of electrodes 121f may be configured to provide enhanced cooling (e.g. internal cooling), promote directional bending, and provide other benefits. Electrodes 121f may deliver unipolar or bipolar energy, such as bipolar energy between neighboring electrodes, or between any pair of electrodes. In an alternative or additional embodiment, electrodes 121f can be configured to create asymmetric steering of the distal portion of shaft 110.

Figure 9C:
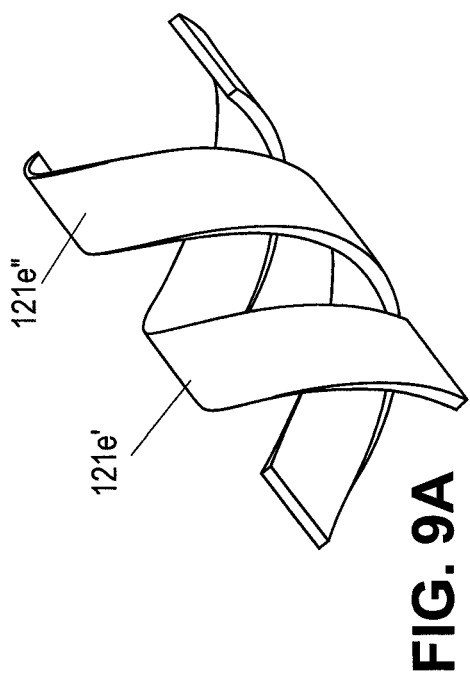
FIG. 9C illustrates a perspective view of a preferred configuration of a tip electrode, with square tip geometry, consistent with the present invention.

Referring specifically to FIG. 9C, a perspective view of tip electrode 131e is shown with a square tip, and flattened sides.

Figure 9D:
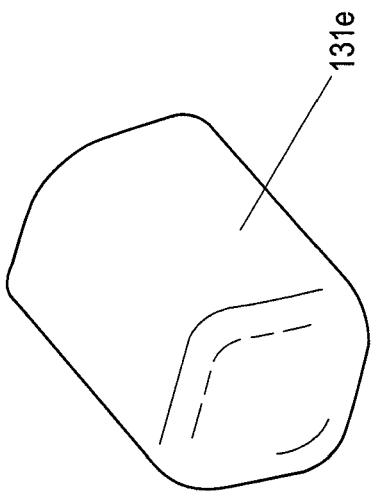
FIG. 9D illustrates a perspective view of a preferred configuration of three shaft electrodes with "S" shape geometry, and a tip electrode with flattened sides, consistent with the present invention.

Referring specifically to FIG. 9D, a perspective view of three "S" shaped band electrodes 121g are shown. The "S" geometry provides enhanced cooling of the electrode due to the large, separated surface areas. Also shown in FIG. 9D is a perspective view of tip electrode 131f that has a rounded tip, but flattened sides.

Referring specifically to FIG. 9E, a side view of shaft electrode 121f is shown. Shaft electrode 121f includes a variable wall thickness, where one end of shaft electrode 121f has a thicker wall than the other end, and a relatively linear taper exists between one end and the other.

Referring specifically to FIG. 9F, a side view of shaft electrode 121g is shown. Shaft electrode 121g includes a variable wall thickness, where each end has a thinner wall than a midpoint location, and a relatively linear taper exists between the midpoint and each end. The outer diameter of shaft electrode 121g is in a relatively constant diameter, while the inner diameter varies to accommodate the increased wall thickness. Alternatively, a similar asymmetric profile is incorporated into a tip electrode of the present invention.

Referring specifically to FIG. 9G, a side view of tip electrode 131h is shown. Tip electrode 131h includes a variable wall thickness, where the wall is thicker at the distal tip, tapering relatively linearly to the proximal end.

Referring specifically to FIG. 9H, a side view of tip electrode 131i is shown. Tip electrode 131i includes a variable wall thickness, where the wall is thicker at the proximal end, tapering relatively linearly to the distal tip.

Referring specifically to FIGS. 9J and 9K, side and end views, respectively, of tip electrode 131j are shown. Tip electrode 131j includes a variable wall thickness, where the cross sectional profile includes a thicker wall on one side than the other. Alternatively, a similar asymmetric profile is incorporated into a shaft electrode of the present invention. The orientation of the asymmetric electrode at the tip or on the shaft may be such that the thicker portion is configured to contact tissue during ablation, such as by being on the outside of a deflecting curve. The thicker and thinner portions can be configured to optimize transfer of heat to circulating blood.

Referring specifically to FIG. 9L, an end view of shaft electrode 121k is shown. Shaft electrode 121k includes a projecting fin 125, oriented radially in toward the center axis of shaft electrode 121k. Projecting fin 125 is configured to provide a heat sink, improving the cooling properties of shaft electrode 121k. Alternatively, a similar projecting fin is incorporated into a tip electrode of the present invention.

Referring specifically to FIG. 9M, an end view of shaft electrode 121m is shown. Shaft electrode 121m includes one or more projecting fins 125, projecting radially out from the center axis of shaft electrode 121m. Projecting fins 125 are configured to provide a heat sink, residing in the blood flow and improving the cooling properties of shaft electrode 121m. In a preferred embodiment, shaft electrode 121m includes a tissue contacting portion without projecting fins, (e.g. on the outside of a deflecting curve geometry), and fins 125 are positioned away from the tissue contacting portion (i.e. the fins 125 are in the flow of blood or otherwise away from the tissue to be ablated). Alternatively, similar one or more outwardly projecting fins are incorporated into a tip electrode of the present invention.

Referring specifically to FIGS. 9N and 9P, a side and end view, respectively, of shaft electrode 121n is shown. Shaft electrode 121n includes a variable wall thickness, where each end has a thinner wall than a midpoint location, and a relatively linear taper exists between the midpoint and each end. The inner diameter of shaft electrode 121g is in a relatively constant diameter, while the outer diameter varies to accommodate the increased wall thickness. Alternatively, a similar asymmetric profile is incorporated into a tip electrode of the present invention.

The ablation elements of the present invention may incorporate the construction features illustrated and described in reference to FIGS. 9A through 9P, singly or in combination. While the varied wall thicknesses of these ablation elements have been accomplished with relatively linear tapers, non-linear variations could be employed. Other variations of non-constant wall thickness, surface modifications such as bumps, dimples, ridges and grooves, and other asymmetries may be incorporated, singly or in combination, and remain within the spirit and scope of this application.

Referring now to FIG. 10, a side view of a distal end of an ablation catheter 100 of the present invention is illustrated. Ablation catheter 100 includes a shaft 110 which includes tip electrode 131 mounted on the distal end of shaft 110, and shaft electrodes 121 mounted to shaft 110, proximal to tip electrode 131. Within the outer diameter of shaft 110 is malleable member 111, such as a plastically deformable wire or band that can be embedded in the wall of shaft 110. Alternatively, malleable member 111 may be maintained in contact with shaft 110 by being captured between shaft 110 and an inner tube such as a liner, or via fastening means such as an adhesive. Malleable member 111 can be configured to be plastically deformed, either by pressing the distal portion of the shaft against tissue, hand manipulation by an operator, and/or by an internal steering mechanism. Malleable member can also be configured to maintain a desired shape, until a restoring force is applied, such as via a steering wire or other steering mechanism, or a straightening force such as a force generated by hydraulics or pneumatics delivered to a distal portion of the shaft 110 via an fluid transfer lumen, not shown. In an alternative embodiment, member 111 is resiliently elastic, such as to resist bending in a first direction (similar to the guide plates described hereabove), or to provide a restoring force which straightens the distal portion of the shaft when no other force is being applied.

Referring now to FIGS. 11A and 11B, a side view of a distal portion of an ablation catheter of the present invention is illustrated. In FIG. 11A, the distal portion is shown in an unexpanded state, and in FIG. 11B the distal portion is shown in an expanded state. The distal end of shaft 110 can include multiple shaft electrodes 121, of a similar construction to the shaft electrodes described throughout this application. For example, the distal end of shaft 110 can be split, and balloon 141 can be mounted between the split ends. Balloon 141 can be fluidly connected to a pressure source, such as a saline source or other fluid source, such as a source activated by a control on a handle of the ablation catheter (fluid source and handle not shown). The ablation catheter of FIGS. 11A and 11B can also be configured to deliver unipolar or bipolar energy, such as bipolar energy delivered between two "parallel" electrodes 121, or any pair of electrodes. Balloon 141 may be a compliant balloon, such that increased inflation pressure continually increases the separation distance of the split end of shaft 110, or balloon 141 may be a non-compliant balloon, such that increased inflation pressure results in minimal increase in the separation distance beyond a fixed distance. Balloon 141 may have an inflated geometry that is relatively parallel and linear as shown in FIG. 11B, or may be configured to create a non-parallel, curved or otherwise non-linear geometry. Balloon 141 may be configured to additionally provide a cooling function, such as a balloon which receives a continuous replacing volume of cool saline, prior to, during and/or after delivery of ablation energy.

Referring now to FIGS. 12A and 12B, a side view of a distal portion of an ablation catheter of the present invention is illustrated. In FIG. 12A, the distal portion is shown in an undeployed state, and in FIG. 12B the distal portion is shown in a deployed, "open V" geometry. Shaft 110 includes expandable carrier assembly 142 comprising two tip electrodes 131a and 131b. The two tip electrodes 131a and 131b may be electrically isolated from each other (e.g. via an insulator located on one or both mating surfaces), or may conduct electricity between the two when in the undeployed condition of FIG. 12A. Unipolar and bipolar energy can be delivered in both the deployed and undeployed states. Advancement of a control shaft, not shown but preferably operably connected to a control on a handle of the ablation catheter, causes electrodes 131a and 131b to assume the "open V" geometry. Shaft 110 can further include one or more shaft electrodes 121, such that bipolar energy can be delivered between electrodes 131a and/or 131b and shaft electrode 121. Alternatively or additionally, shaft electrode 121 may deliver unipolar energy. In a preferred method, carrier assembly 142 is deployed as shown in FIG. 12B, and shaft 110 is advanced such that tissue is positioned between electrodes 131a and 131b. Unipolar energy can be delivered from either or both electrodes 131a and 131b, and bipolar energy can be delivered between electrodes 131a and 131b.

Referring now to FIGS. 13 and 14, a side sectional view of a distal portion of an ablation catheter of the present invention is illustrated. Shaft 110 can include a tapered profile transitioning from a larger diameter section, through tapered joint 113, to a smaller diameter section having a steerable portion, as has been described in detail above in reference to various embodiments of the present invention. Shaft 110 may include symmetric or asymmetric steering, also described in detail hereabove in reference to various embodiments of the present invention. Steering wires 115 can be "free floating" in the larger diameter portion of shaft 110, and frictionally attached to shaft 110 in the smaller diameter portion, such as a frictional engagement caused by embedded steering wires 115 in the wall of the smaller diameter portion, or sandwiching steering wires 115 between a liner and the inner wall of shaft 110. Steering wires 115 are operably attached to one or more controls, such as a rotating knob on the handle of the catheter, handle and controls not shown but described in detail above.

At the distal end of shaft 110 is tip electrode 131, preferably adhesively mounted to shaft 110 as well as crimped or swaged on its proximal end. Attached to an inside wall of tip electrode 131 is a signal wire 117a and thermocouple 139. Proximal to tip electrode 131 is at least one shaft electrode 121, preferably attached to shaft 110 with adhesive, and in a preferred embodiment, further attached by crimping one or both ends of shaft electrode 121. Signal wires 117b can pass through a hole (e.g. a laser cut hole) in the wall of shaft 110 (as well as through any liners, braids, or other internal structures). Attached to an inside wall of shaft electrode 121 is a signal wire 117b and thermocouple 138.

Referring now to FIGS. 15, 15A, 15B, 15C, 15D, 15E and 15F, an ablation catheter of the present invention is illustrated, where an advanceable carrier assembly can be deployed from the catheter's distal end. Referring to FIG. 15, ablation catheter 100 includes a handle 150 on the proximal end of shaft 110. Handle 150 includes trigger grip 154 configured to provide an ergonomic holding surface for an operator of ablation catheter 100. Also included in handle 150 is jack 155, electrically connected to one or more ablation elements of catheter 100 such as shaft electrodes 120. On the distal end of shaft 110 is a deployable carrier assembly, distal ablation assembly 130, which is operably attached to knob 151 of handle 150. Ablation catheter 100 further includes capture device 300, removably engaged with handle 150 and configured to provide a strain relief between the proximal end of shaft 110 and handle 150, as well as perform a capture function for introducing the distal end of ablation catheter 100 into a percutaneous sheath, such as a sheath placed in the femoral vein of a patient.

Referring now to FIG. 15A, distal ablation assembly 130, shown in its deployed state, is attached to control shaft 119, which is operably attached to knob 151 of handle 150. Signal wires 117 are attached to one or more ablation elements of distal ablation assembly 130 as well as shaft electrodes 121. Shaft electrodes 121 are adhesively other otherwise attached to shaft 110, and include fillets 122 at either end. Within a lumen of shaft 110 is tube 127, which surrounds signal wires 117 such as to protect signal wires 117 from damage. On the proximal end of shaft 110 is strain relief 126, preferably heat shrink tubing surrounding shaft 110. Steering wires 115 travel within the OD of shaft 110 such as to facilitate symmetric or asymmetric steering of the distal portion of shaft 110.

Referring now to FIGS. 15B, 15C and 15D, the distal end of shaft 1110 is shown. In FIG. 15B, a side view of the distal end of shaft 110 is shown with distal ablation assembly 130 in its undeployed state. In FIG. 15C, a side view of the distal end of shat 110 is shown with distal ablation assembly 130 in its deployed state. Distal ablation assembly 130 includes four carrier arms 133, each of which includes a distal electrode 131. Alternatively, the distal ablation assembly can comprise only two carrier arms which overlap to form the assembly shown in FIG. 15D. Unipolar or bipolar RF energy can be transmitted to tissue by anyone of distal electrodes 131 and/or shaft electrodes 121. Bipolar energy can be transmitted between any pair of distal electrodes 131 and/or shaft electrodes 121. FIG. 15D illustrates an end view of the deployed condition of FIG. 15C.

Referring now to FIGS. 15E and 15F, a preferred shape of distal electrodes 131 is illustrated. The pie shape provides for an efficient, compacted or reduced volume (i.e. minimal open space between components) when distal ablation assembly 130 is in the undeployed condition of FIG. 15B. As shown in FIGS. 15E and 15F, a through-hole may be included in electrode 131 such as to pass carrier arm 133 through, and/or to pass one or more signal wires through.

Figure 16:
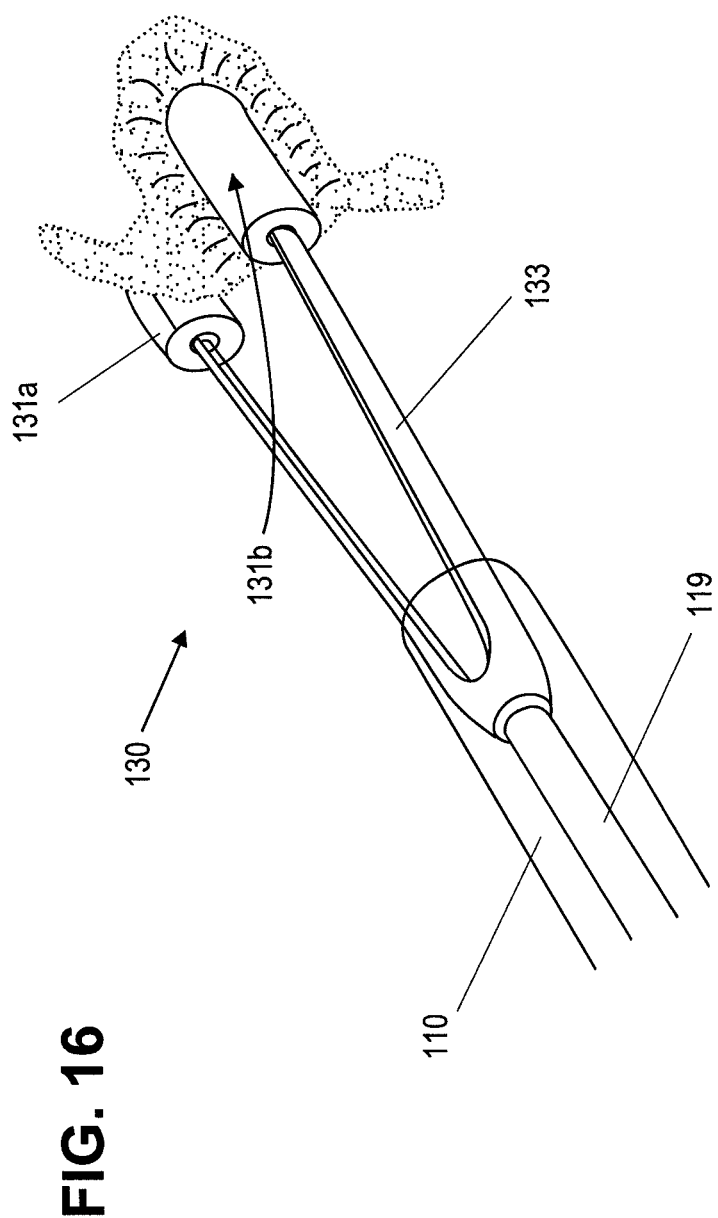
FIG. 16 illustrates a perspective view of the distal portion of an ablation catheter including a carrier assembly configured in a forked geometry and advanceable from the distal end of the catheter shaft, consistent with the present invention.

Referring now to FIG. 16, an ablation catheter of the present invention is illustrated, where an advanceable carrier assembly can be deployed from the distal end. Shaft 110 surrounds control shaft 119 which can be advanced and retracted, such as a retraction which causes distal ablation assembly 130 to be contained within the lumen of shaft 110, and an advancement which causes distal ablation assembly 130 to exit the distal end of shaft 110, expanding to a fork shaped condition. Distal ablation assembly 130 can include two carrier arms 133, and at the end of each carrier arm is distal electrode 131 a and 131b. Distal ablation assembly can be partially deployed, as shown in FIG. 16, such that the two carrier arms 133 have a reduced (more acute) angle as compared to the condition where control shaft 119 is further advanced. Slight advancements and retractions of control shaft 119 cause the angle between the two carrier arms to increase and decrease respectively. In a preferred method, control shaft 119 is advanced to cause a sufficient angle to surround a portion of tissue, and subsequent retraction causes carrier arms 133 and electrodes 131a and 131b to "pinch" or otherwise capture the targeted tissue. In the pinched state, unipolar and/or bipolar (between electrodes 131a and 131b) can be delivered to create a precision lesion in the tissue. A steering mechanism, such as a symmetric or asymmetric steering mechanism may be included. In a preferred embodiment, at least one thermocouple is included in each electrode 13a and 131b. Although distal ablation assembly 130 is shown with two carrier arms 133, alternative embodiments include three or more carrier arms 133.

Figure 17C:
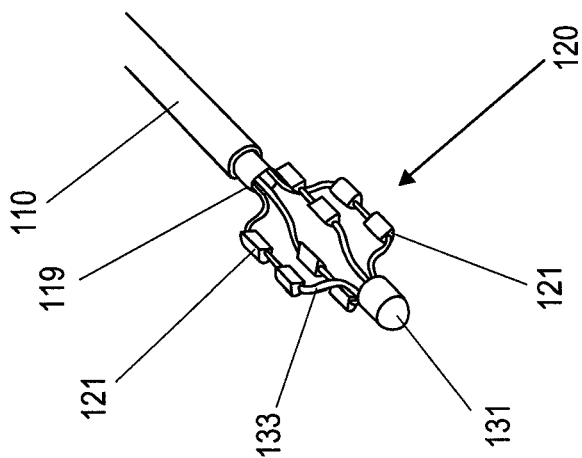
FIGS. 17A, 17B and 17C illustrate perspective views of the distal portion of an ablation catheter in deployed, partially deployed, and fully deployed states, respectively, consistent with the present invention.
Figure 17B:
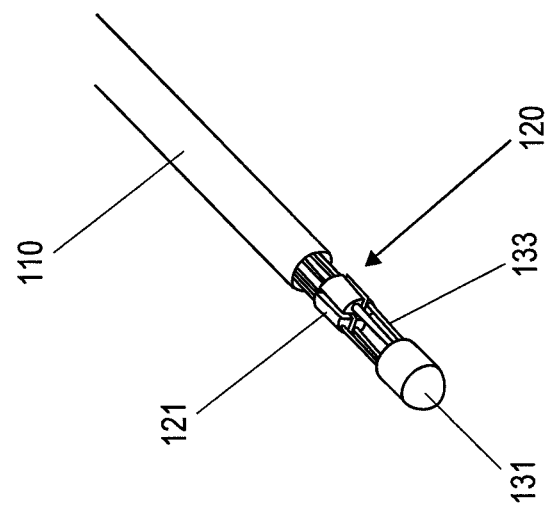
Figure 17A:
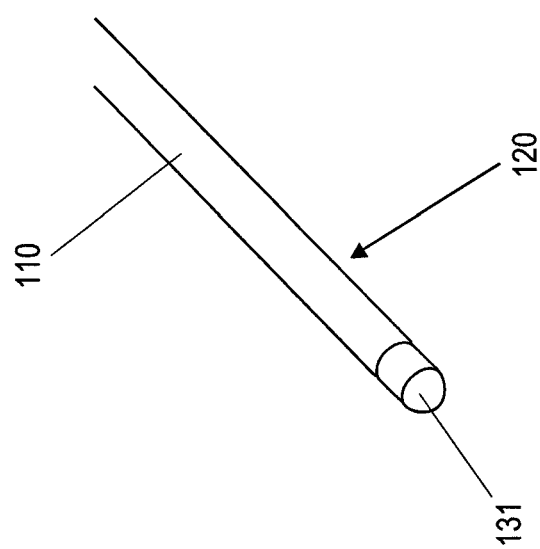

Referring now to FIGS. 17A, 17B and 17C, the distal portion of an ablation catheter of the present invention is illustrated including an advanceable carrier assembly deployable from the distal end. Shaft 110 can surround control shaft 119 which can be advanced and retracted, such as a retraction which causes shaft ablation assembly 120 to be contained within a lumen of shaft 110, and an advancement which causes shaft ablation assembly 120 to exit the distal end of shaft 110, and expand to the geometry shown in FIG. 17C. Shaft ablation assembly 120 includes four carrier arms 133 upon which at least one electrode 121 is fixedly attached (two electrodes 121 on each carrier arm shown). Electrodes 121 preferably have a pie or wedge shape to allow efficient volume compression when in the undeployed state. At the end of the four carrier arms 133 is tip electrode 131.

FIG. 17A shows the control shaft fully retracted, shaft ablation assembly contained within a lumen of shaft 110, and tip electrode 131 located at the distal end of shaft 131. In this configuration, energy can be delivered from tip electrode 131 (e.g. unipolar RF energy). FIG. 17B shows the control shaft partially or fully advanced, prior to expansion of carrier arms 133 and shaft ablation assembly 120. FIG. 17C shows the control shaft in the fully advanced condition, with carrier arms 133 and shaft ablation assembly 120 fully expanded. Unipolar or bipolar energy can be delivered by and between distal electrode 131 and electrodes 121 (e.g. bipolar RF energy between any electrode pair). The ablation catheter of FIGS. 17A, 17B and 17C include signal wires, not shown, but electrically connected to tip electrode 131 and electrodes 121. A steering mechanism, such as a symmetric or asymmetric steering mechanism may be included. In a preferred embodiment, at least one thermocouple is included in each electrode 121. In another preferred embodiment, at least two thermocouples are included in tip electrode 131. Although shaft ablation assembly 120 is shown with four carrier arms 133, alternative embodiments include two, three, or more than four carrier arms 133.

Referring now to FIGS. 18A, 18B, 18C and 18D, an ablation catheter of the present invention is illustrated, where a carrier assembly can be transitioned from a near linear state, to an expanded state. In the linear state, two carrier arms 133 are relatively linear and parallel to one another, and reside at a location distal to the distal end of shaft 110. A control shaft 119 can reside between the two carrier arms 133, and includes tip electrode 131 at its distal end. The proximal end of control shaft 119 can be operably attached to a control on a handle of the ablation catheter (handle and control not shown but described in detail hereabove). Retraction of control shaft 119 can cause the two carrier arms 133 to bow radially outward as shown in FIG. 18D. Advancement of control shaft 119 can cause the two carrier arms 133 to transition to the near linear state shown in FIG. 18A.

Mounted to the two carrier arms 133 are electrodes 121, preferably shown in the staggered configuration shown in FIG. 18A, such as to allow compact volume when carrier arms 133 are in the linear state. Electrodes 121 are configured in the partial band construction shown in FIGS. 18B and 18C. Energy can be deployed in the linear or expanded conditions.

Referring now to FIGS. 19A, 19B, 19C, 19D and 19E, an ablation catheter of the present invention is illustrated, where a carrier assembly can be transitioned from a near linear state, to an expanded state. In the linear state, two carrier arms 133 are relatively linear and parallel to one another, and each consist of approximately one-half of shaft 110' which has been slit at a location near the distal end, the slit 1000 traveling proximally such as to create the desired deployed geometry (e.g. desired deployed diameter). A control shaft 119 resides between the two carrier arms 133, and includes tip electrode 131 at its distal end. The proximal end of control shaft 119 is operably attached to a control on a handle of the ablation catheter (handle and control not shown but described in detail hereabove). Retraction of control shaft 119 causes the mid portions of the two carrier arms 133 to bow radially outward as shown in FIG. 19E. Advancement of control shaft 119 causes the two carrier arms 133 to transition to the near linear state shown in FIG. 19D.

Mounted to the two carrier arms 133 are electrodes 121, shown in the staggered configuration of FIG. 19D, but alternatively one or more electrodes 121 may be adjacent the other. Electrodes 121 are configured in the half band construction shown in FIG. 18C. Tip electrode 131 is shown in the reduced proximal flange, rounded distal tip construction shown in FIG. 19B. FIG. 19A shows shaft 110' with a slit 1000 allowing expansion of carrier arms 133. FIG. 19A shows electrodes 131 and 121 removed, and the lumen (for insertion of tip electrode 131) and recesses 128 (for attachment of shaft electrodes 121). Energy can be deployed in the linear or expanded conditions.

Figure 20A:
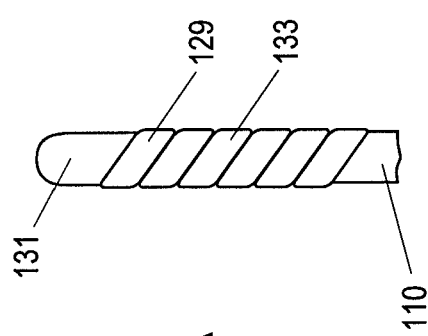
FIGS. 20A and 20B illustrate side and perspective views, respectively, of the distal portion of an ablation catheter with a spiral carrier arm and an elongate electrode, consistent with the present invention.
Figure 20B:
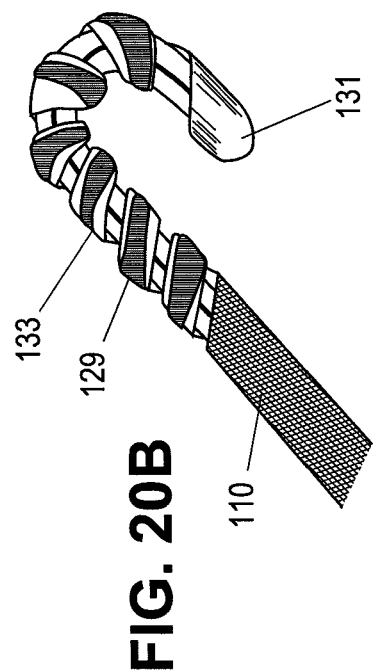

Referring now to FIGS. 20A, and 20B, an ablation catheter of the present invention is illustrated including a carrier assembly configured to be transitioned from a compact spiral state to an expanded spiral state. Carrier arm 133 can include tip electrode 131 at its distal end, and a filament electrode 129 along a majority of its length. In the compact state shown in FIG. 20A, carrier arm 133 is shown in a tight spiral. Advancement or retraction of one or more control shafts, not shown, causes the spiral to unfurl as shown in FIG. 20B. Also as shown in FIG. 20B, carrier arms 133 may deflect such as to assume the candy-cane geometry depicted. Energy can be delivered in the compact or expanded state, and can be delivered from either or both the tip electrode 131 and filament electrode 129, in either unipolar or bipolar mode.

Figure 21A:
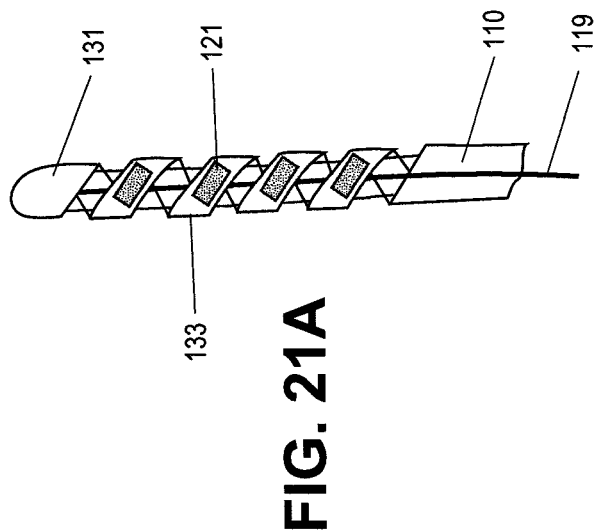
FIGS. 21A and 21B illustrate side and perspective views, respectively, of the distal portion of an ablation catheter with a spiral carrier arm and multiple discrete electrodes, consistent with the present invention.
Figure 21B:
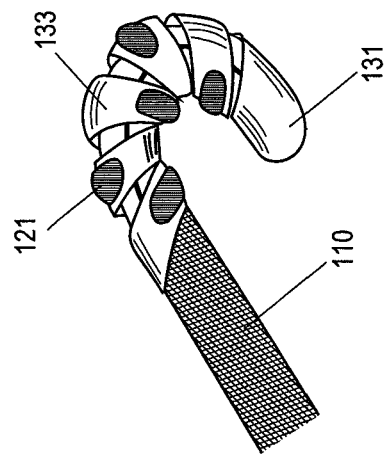

Referring now to FIGS. 21A, and 21B, an ablation catheter of the present invention is illustrated including a carrier assembly configured to transition from a compact spiral state to an expanded spiral state. Carrier arm 133 can include tip electrode 131 at its distal end, and two or more discrete electrodes 121 along its length. In the partially expanded shown in FIG. 20A, carrier arm 133 is unfurled from a compact state, not shown. Advancement or retraction of control shaft 119 can cause the spiral to expand and contract. The distal end of the ablation catheter may also deflect, as shown in FIG. 21B, to assume the candy-cane geometry depicted. Energy can be delivered in the compact or expanded state, and can be delivered from any of the tip electrode 131 and discrete electrodes 121, in either unipolar or bipolar mode.

Referring now to FIGS. 22A, and 22B, an asymmetrically bending shaft of the present invention is illustrated. Shaft 110 includes multiple wedges 134 along its length. Wedges 134 may be pie shaped, as shown in FIG. 22B, cube shaped, or configured in another geometry. In a preferred embodiment, wedges 134 are constructed of a softer material than the material of shaft 110, such that deflection toward the base of each triangle wedge 134 is a smaller radius than deflection toward the peak of each triangle, as shown in FIG. 22B. Shaft 110 may include multiple levels of stiffness along its length, e.g. by materials of two different durometers. In a preferred configuration, a proximal section of the shaft is stiffer than a distal section of the shaft, and the distal section of the shaft is stiffer than the wedges 134.

Referring now to FIGS. 23A, 23B and 23C, an asymmetrically bending shaft of the present invention is illustrated. Shaft 110 includes multiple wedges 134a and 134b along its length. Wedges 134a and 134b include different geometries such as to cause a complex deflection pattern when a deflection force is applied to the portion of shaft 110 including wedges 134a and 134b. In the embodiment depicted in FIG. 23A, wedge 134a has a symmetric, rectangular profile and wedge 134b has an eccentric, partial spherical geometry. Combinations of wedge 134a and 134b can be used to create one or more complex deflection geometries, including both symmetric and asymmetric deflection geometries as have been described above. In a preferred embodiment, a deflection in a first direction results in a small radius of curvature, as shown in FIG. 23B, and a deflection in the opposite direction results in a larger radius of curvature, as shown in FIG. 24C. In a preferred embodiment, wedges 134a and 134b are less rigid (have softer durometers) than the portion of shaft 110 proximate each wedge, such as to create a symmetric or asymmetric hinge. In an alternative embodiment, wedges 134a and/or 134b are stiffer than the neighboring shaft 110 material, and a hinge is created in the shaft 110 portion between two wedges. Wedges 134a and/or 134b may be constructed and positioned such as to create a preferred deflection direction, such as to avoid bending in an undesired direction.

Figure 24:
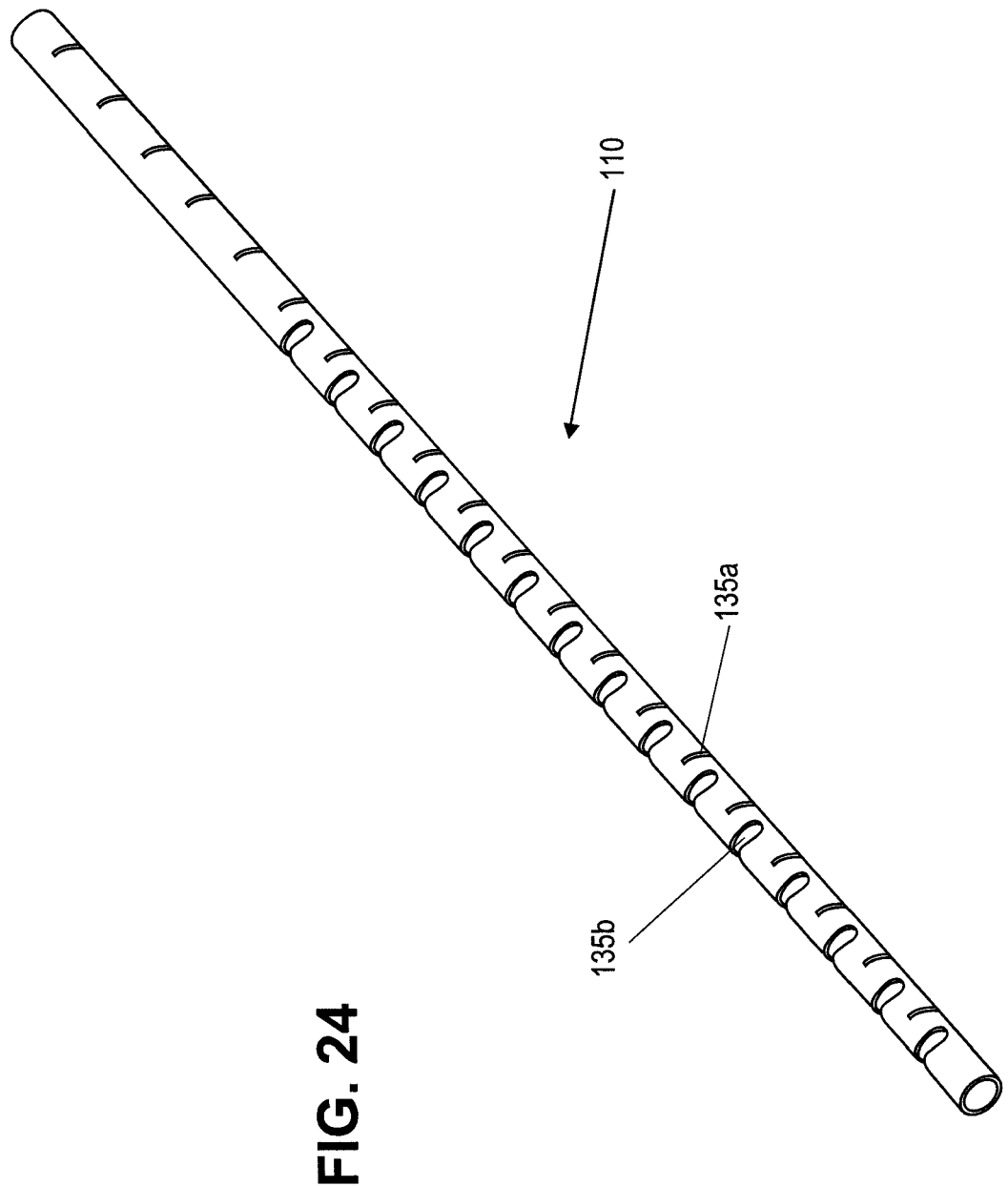
FIG. 24 illustrates a perspective view of an asymmetrically deflectable catheter shaft construction including one or more slits, consistent with the present invention.

Referring now to FIG. 24, an asymmetrically bending shaft 110 of the present invention is illustrated. FIG. 24 depicts a method for steering the distal end of the catheter and maintaining the planarity of the distal portion during operator induced deflection (when being steered). Shaft 110 includes multiple slits, 135a and 135b along its length. Slits 135a can be positioned along one side of shaft 110, and slits 135b can be on the opposite side of shaft 110 (e.g. approximately 180° apart). Slits 135b can be of larger width than slits 135a, such that the bending force required to curve toward the side that slits 135b are positioned is less than the bending force required to curve toward the side that slits 135a. In the configuration shown, the radius formed in curving toward the side that slits 135b are positioned, will be smaller than the radius formed in curving toward the side that slits 135a are positioned (e.g. asymmetric deflection at similar deflection force). Slits 135a and slits 135b further provide preferential bending, in other words bending in the two directions aligned toward the sides that either slits are positioned is preferred versus bending in a different direction. The segments of shaft 110 that are stiffer (e.g. not cut) act as a spine keeping the bending in a single plane. In addition, the slits on one side of this steering mechanism can be different in geometry (e.g. size) from the slits on the opposite side. By making the slits on each side different, the distal portion of shaft 110 can deflect with two different sized curves (e.g. curve formed by bending in a first direction, and curve formed by bending in a direction 180° from the first direction). Shaft 110 or FIG. 24 may be covered by an outer tube, such as a liner, to avoid sharp edges on the outer diameter of the ablation catheter. Alternatively or additionally, slits 135*a* and/or slits 135*b* may be filled with a material, such as a material softer than the material of shaft 110.

Figure 25:
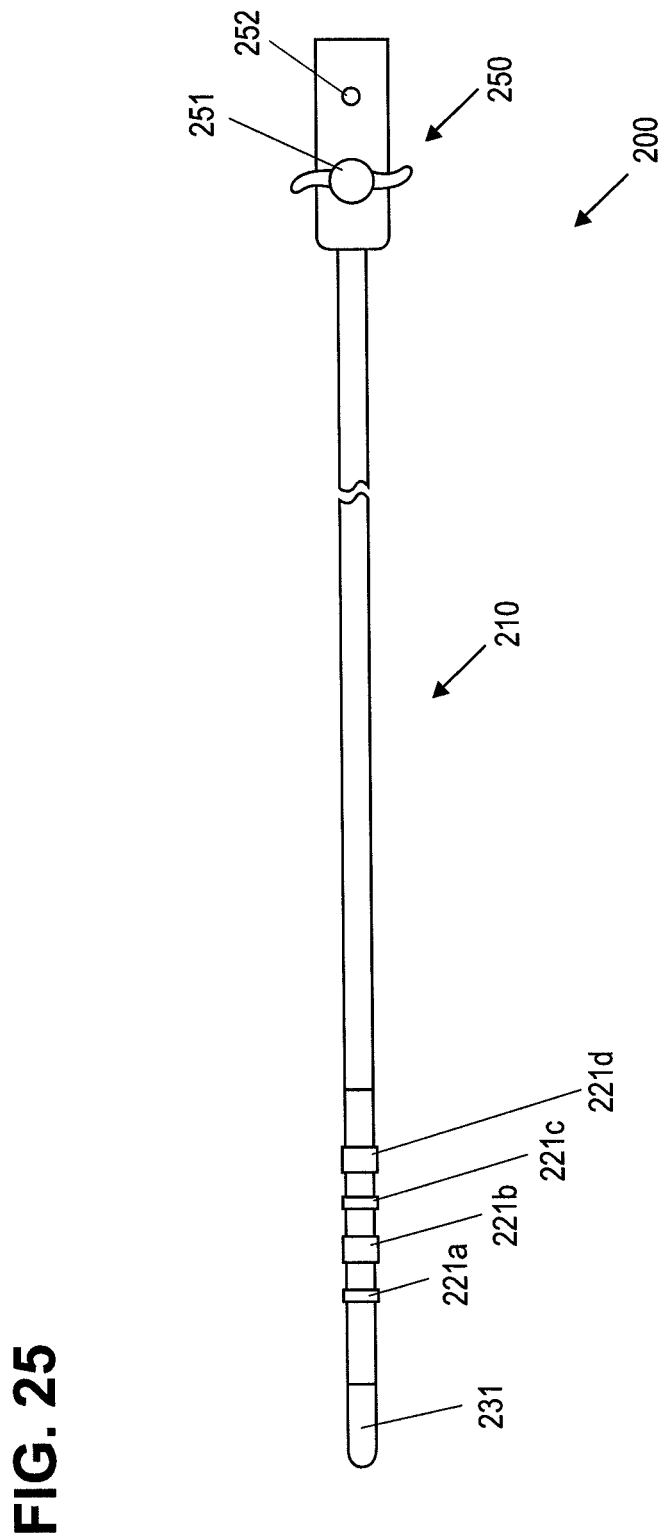
FIG. 25 illustrates a side view of a catheter, including at least one tip functional element, at least of shaft functional element and a deflectable distal portion, consistent with the present invention.

Referring now to FIG. 25, a preferred embodiment of a percutaneous treatment and/or diagnostic catheter of the present invention is illustrated. Catheter 200 can include flexible shaft 210. Handle 250 can be located on the proximal end the shaft and can include multiple controls, such as knob 251 and button 252. Button 252 can be configured to initiate and/or discontinue one or more functions of catheter 200. Knob 251 can be configured, when rotated, to cause distal portion of the shaft to deflect in one or more directions, such as to curve in one direction when rotated clockwise, and another direction when rotated counter-clockwise. In a preferred embodiment, described in detail above, knob 251 can be attached to two steering wires which are captured in the distal portion of the shaft and cause bi-directional steering such as symmetric or asymmetric steering, also described in numerous embodiments above. In alternative embodiments, 1, 3, 4 or more steering wires may be incorporated, such as steering wires separated by approximately 120° or 90°, causing deflection in a single plane, or two or more planes. Each deflection may have a simple geometry such as a single plane, fixed radius curve, or more complex geometries such as bending in 3-D space.

Additional controls may be integrated into handle 250 to perform additional functions. A connector, not shown, can be integral to handle 150 to allow electrical, mechanical (e.g. mechanical linkage or fluid injection) or other connections from ablation catheter 100 to one or more other medical or other devices.

The shaft can also include multiple shaft functional elements 221*a*, 221*b*, 221*c* and 221*d*. The shaft can further include tip functional element 231, such as an atraumatic (e.g. rounded tip), functional element. In an alternative embodiment, tip functional element 231 may include multiple functional elements.

In a preferred embodiment, the functional elements of catheter 200 can be attached to conduits such as signal wires, fluid delivery tubes, optical fibers or other conduits, not shown but traveling within shaft 210 and connecting to a mechanism within handle 250 and/or a connector on handle 250.

Functional elements of catheter 200 can include but are not limited to sensors; transducers and combinations thereof. Transducers include but are not limited to: electrodes such as platinum electrodes configured to deliver energy and receive electro grams; sound transducers such as ultrasonic, acoustic and subsonic transducers; drug delivery elements; radiation sources, magnetic sources; heat generators; cooling or cryogenic transducers such as a cooling element connected to a conduit through which cooling liquid passes near an ablation element; other transducers and combinations thereof. Sensors include but are not limited to: temperature sensors such as thermocouples; blood sensors such as blood gas sensors or blood glucose sensors; respiration sensors; fluid flow sensors such as blood flow sensors; pH sensors; pressure sensors; other sensors and combinations thereof. In a preferred embodiment, catheter 200 of FIG. 25 is configured to transition between two asymmetric deflection geometries as has been described in reference to numerous figures above.

Figure 26B:
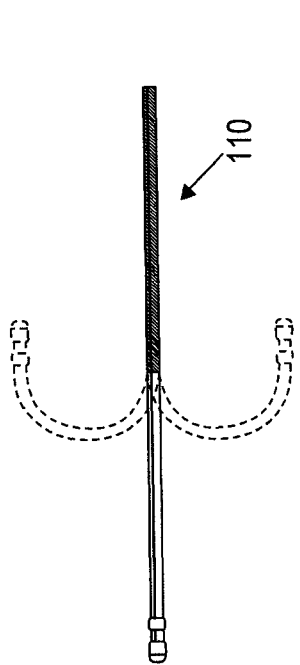
FIG. 26B illustrates a side view of the distal portion of a shaft configured to deflect in two directions with two preferred symmetric deflection geometries, consistent with the present invention.
Figure 26D:
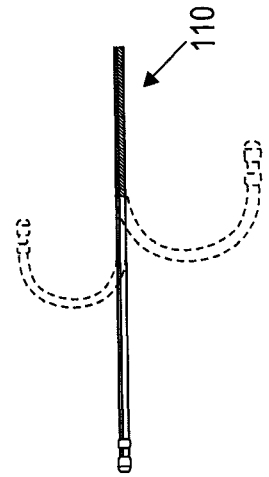
FIG. 26D illustrates a side view of a distal portion of a shaft configured to deflect in two directions with two preferred asymmetric deflection geometries, consistent with the present invention.
Figure 26A:
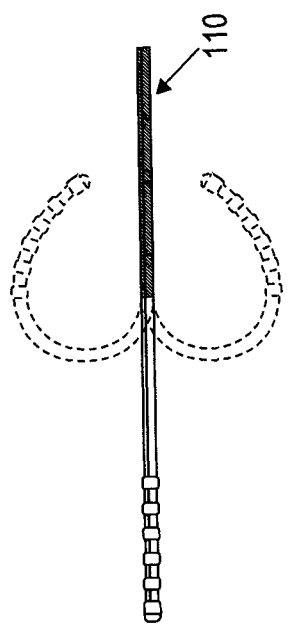
FIG. 26A illustrates a side view of the distal portion of a shaft configured to deflect in two directions with two preferred symmetric deflection geometries, consistent with the present invention.
Figure 26C:
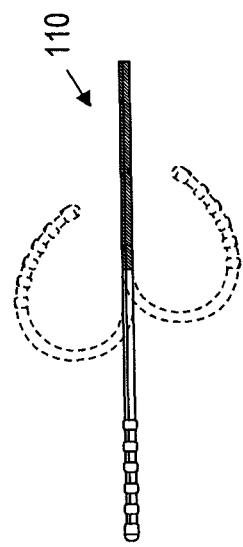
FIG. 26C illustrates a side view of the distal portion of a shaft configured to deflect in two directions with two preferred asymmetric deflection geometries, consistent with the present invention.

Referring now to FIGS. 26A, 26B, 26C and 26D, symmetrically and asymmetrically bending shafts of the present invention are illustrated. Each of the shafts can include multiple functional elements, such as electrodes, in the deflecting portion. Each of the shafts also can include an additional functional element located at the distal end of shaft 110. FIG. 26A depicts a preferred symmetrically deflecting shaft 110 which can deflect in a curve in two directions with the same geometry (e.g., deflect with a curve of approximately 24 mm). FIG. 26B depicts a preferred symmetrically deflecting shaft 110 which can deflect in a curve larger than that of FIG. 26A, in two directions with the same geometry (e.g., deflect with a curve of approximately 28 mm). FIG. 26C depicts a preferred asymmetrically deflecting shaft 110 which deflects in a smaller curve in a first direction (e.g., deflect with a curve of approximately 24 mm) and in a larger curve in a second direction (e.g., deflect with a curve of approximately 28 mm). FIG. 26D depicts a preferred asymmetrically deflecting shaft 110 which deflects with different geometries than that described above, such as in an approximately 28 mm curve in a first direction and in an approximately 38 mm curve in a second direction.

It should be understood that numerous other configurations of the systems, devices and methods described herein can be employed without departing from the spirit or scope of this application. Numerous figures have illustrated typical dimensions, but it should be understood that other dimensions can be employed which result in similar functionality and performance.

It should be understood that the system includes multiple functional components, such as the RF generator and various ablation catheters of the present invention. A preferred ablation catheter consists of a catheter shaft, a shaft ablation assembly including at least one shaft ablation element, and a distal ablation assembly including at least one tip ablation element.

The ablation catheters of the present invention may include a steerable outer sheath, or may work in conjunction as a system with a separate steerable outer sheath. One or more tubular components of the ablation catheter may be steerable such as with the inclusion of a controllable pull wire at or near the distal end. The ablation catheters of the present invention may be inserted over the wire, such as via a lumen within one of the tubular conduits such as within a lumen of the tubular body member or control shaft, or alternatively the catheter may include a rapid exchange sidecar at or near its distal end, consisting of a small projection with a guidewire lumen therethrough. A guidewire lumen may be included solely for the guidewire, or may provide other functions such as a vacuum lumen for an integral suction port integrated at the distal portion of the carrier assembly.

The ablation catheters of the present invention include one or more ablation elements. In preferred embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radio frequency energies; thermal energy such as heat and cryogenic energies; chemical energy; light energy such as infrared and visible light energies; mechanical energy; radiation; and combinations thereof. The RF generator of the present invention may further provide one of the additional energy forms described immediately hereabove, in addition to the RF energy.

One or more ablation elements may comprise a drug delivery pump or a device to cause mechanical tissue damage such as a forwardly advance able spike or needle. The ablation elements can deliver energy individually, in combination with or in serial fashion with other ablation elements. The ablation elements can be electrically connected in parallel, in series, individually, or combinations thereof. The ablation catheter may include cooling means, such as fins or other heat sinking geometries, to prevent undesired tissue damage and/or blood clotting. The ablation elements may be constructed of various materials, such as plates of metal and coils of wire for RF energy delivery. The electrodes can take on various shapes including shapes used to focus energy such as a horn shape to focus sound energy, and shapes to assist in cooling such as a geometry providing large surface area. Wires and other flexible conduits are attached to the ablation elements, such as electrical energy carrying wires for RF electrodes or ultrasound crystals, and tubes for cryogenic delivery.

The ablation catheter of the present invention preferably includes a handle activating or otherwise controlling one or more functions of the ablation catheter. The handle may include various knobs or levers, such as rotating or sliding knobs which are operably connected to advanceable conduits, or are operably connected to gear trains or cams which are connected to advanceable conduits. These controls, such as knobs use to deflect a distal portion of a conduit, or to advance or retract the carrier assembly, preferably include a reversible locking mechanism such that a particular tip deflection or deployment amount can be maintained through various manipulations of the system.

The ablation catheter may include one or more sensors, such as sensors used to detect chemical activity; light; electrical activity; pH; temperature; pressure; fluid flow or another physiologic parameter. These sensors can be used to map electrical activity, measure temperature, or gather other information that may be used to modify the ablation procedure. In a preferred embodiment, one or more sensors, such as a mapping electrode, can also be used to ablate tissue.

Numerous components internal to the patient, such as the ablation elements, catheter shaft, shaft ablation assembly, distal ablation assembly, carrier arms or carrier assembly, may include one or more markers such as radiopaque markers visible under fluoroscopy, ultrasound markers, magnetic markers or other visual or other markers.

Selection of the tissue to be ablated may be based on a diagnosis of aberrant conduit or conduits, or based on anatomical location. RF energy may be delivered first, followed by another energy type in the same location, such as when a single electrode can deliver more than one type of energy, such as RF and ultrasound energy. Alternatively or additionally, a first procedure may be performed utilizing one type of energy, followed by a second procedure utilizing a different form of energy. The second procedure may be performed shortly after the first procedure, such as within four hours, or at a later date such as greater than twenty-four hours after the first procedure. Numerous types of tissue can be ablated utilizing the devices, systems and methods of the present invention. For example, the various aspects of the invention have application in procedures for ablating tissue in the prostrate, brain, gall bladder, uterus, other organs and regions of the body, and a tumor, preferably regions with an accessible wall or flat tissue surface. In the preferred embodiment, heart tissue is ablated, such as left atrial tissue.

In another preferred embodiment of the system of the present invention, an ablation catheter and a heat sensing technology are included. The heat sensing technology, includes sensor means that may be placed on the chest of the patient, the esophagus or another area in close enough proximity to the tissue being ablated to directly measure temperature effects of the ablation, such as via a temperature sensor, or indirectly such as through the use of an infrared camera. In these embodiments, the RFG includes means of receiving the temperature information from the heat sensing technology, similar to the handling of the temperature information from thermocouples of the ablation catheters. This additional temperature information can be used in one or more algorithms for power delivery, as has been described above, and particularly as a safety threshold which shuts off or otherwise decreased power delivery. A temperature threshold will depend on the location of the heat sensing technology sensor means, as well as where the ablation energy is being delivered. The threshold may be adjustable, and may be automatically configured.

Numerous kit configurations are also to be considered within the scope of this application. An ablation catheter is provided with one or more tip electrodes, one or more shaft electrodes and a shaft with a deflectable distal portion, such as an asymmetrically deflectable distal portion.

Though the ablation device has been described in terms of its preferred endocardial and percutaneous method of use, the ablation elements may be used on the heart during open heart surgery, open chest surgery, or minimally invasive thoracic surgery. Thus, during open chest surgery, a short catheter or cannula carrying the ablation elements may be inserted into the heart, such as through the left atrial appendage or an incision in the atrium wall, to apply the ablation elements to the tissue to be ablated. Also, the ablation elements may be applied to the epicardial surface of the atrium or other areas of the heart to detect and/or ablate arrhythmogenic foci from outside the heart.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with anyone or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:
1. A medical device, the device comprising:
an elongate body defining a distal end and a longitudinal axis
a treatment assembly extending beyond the distal end of the elongate body, the treatment assembly including four carrier arms, each carrier arm including a distal portion, the treatment assembly being selectively transitionable between a delivery configuration and an expanded configuration; and
an electrode coupled to the distal portion of each carrier arm, each electrode defining a proximal end and a distal end and having a pie-shaped cross section, the distal ends of the electrodes being in contact with each other at a point that substantially lies in the longitudinal axis of the elongate body when the treatment assembly is in the expanded configuration.

\* \* \* \* \*